US010405965B2

(12) United States Patent
Kelly

(10) Patent No.: US 10,405,965 B2
(45) Date of Patent: Sep. 10, 2019

(54) PARARENAL AND THORACIC ARCH STENT GRAFT AND METHODS FOR USE

(71) Applicant: Sanford Health, Sioux Falls, SD (US)

(72) Inventor: Patrick W. Kelly, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 50 days.

(21) Appl. No.: 15/080,556

(22) Filed: Mar. 24, 2016

(65) Prior Publication Data

US 2016/0278910 A1    Sep. 29, 2016

Related U.S. Application Data

(60) Provisional application No. 62/138,299, filed on Mar. 25, 2015, provisional application No. 62/197,304, filed on Jul. 27, 2015.

(51) Int. Cl.
*A61F 2/07*    (2013.01)
*A61F 2/852*   (2013.01)
*A61F 2/95*    (2013.01)
*A61F 2/82*    (2013.01)
*A61F 2/06*    (2013.01)

(52) U.S. Cl.
CPC ............... *A61F 2/07* (2013.01); *A61F 2/852* (2013.01); *A61F 2/95* (2013.01); *A61F 2002/061* (2013.01); *A61F 2002/065* (2013.01); *A61F 2002/067* (2013.01); *A61F 2002/826* (2013.01); *A61F 2002/828* (2013.01); *A61F 2220/0033* (2013.01); *A61F 2250/0039* (2013.01)

(58) Field of Classification Search
CPC .... A61F 2/95; A61F 2/07; A61F 2/852; A61F 2002/061; A61F 2002/065; A61F 2002/826; A61F 2250/0039; A61F 2220/0033; A61F 2002/828; A61F 2002/067
See application file for complete search history.

(56) References Cited

U.S. PATENT DOCUMENTS 6,306,164 B1    10/2001  Kujawski
6,325,819 B1 *  12/2001  Pavcnik ................ A61F 2/07
                                              606/108

(Continued)

FOREIGN PATENT DOCUMENTS

WO    2014/172501    10/2014
WO    2015/116715    8/2015

OTHER PUBLICATIONS

International Search Report PCT/US2014/043651, dated Oct. 8, 2014.

(Continued)

*Primary Examiner* — Todd J Scherbel
*Assistant Examiner* — Brooke Nicole Labranche
(74) *Attorney, Agent, or Firm* — McDonnell Boehnen Hulbert & Berghoff LLP

(57) ABSTRACT

Example stent grafts and methods for placement thereof are provided. An example stent graft may include (a) a main body stent graft defining a lumen that has a first end and a second end, (b) a diaphragm coupled to the main body stent graft, where the diaphragm defines at least three openings and (c) at least three stent graft extensions each defining a lumen, where a first end of each of the three stent graft extensions is coupled to one of the three openings.

15 Claims, 27 Drawing Sheets

(56) References Cited

U.S. PATENT DOCUMENTS

| | | |
|---|---|---|
| 6,585,756 B1 | 7/2003 | Strecker |
| 6,635,080 B1 | 10/2003 | Lauterjung et al. |
| 6,942,692 B2 | 9/2005 | Landau et al. |
| 7,014,653 B2 | 3/2006 | Ouriel et al. |
| 7,122,052 B2 | 10/2006 | Greenhalgh |
| 8,105,372 B1 | 1/2012 | Chuter |
| 8,845,714 B2 | 9/2014 | DiMatteo et al. |
| 8,998,971 B1 * | 4/2015 | Kelly ................. A61F 2/07 623/1.11 |
| 2002/0058986 A1 | 5/2002 | Landau et al. |
| 2002/0058993 A1 | 5/2002 | Landau et al. |
| 2002/0169497 A1 | 11/2002 | Wholey et al. |
| 2003/0120330 A1 | 6/2003 | Ouriel et al. |
| 2003/0130720 A1 | 7/2003 | DePalma et al. |
| 2004/0073288 A1 | 4/2004 | Kerr |
| 2004/0193245 A1 | 9/2004 | Deem et al. |
| 2006/0184228 A1 | 8/2006 | Khoury et al. |
| 2006/0229709 A1 * | 10/2006 | Morris ................. A61F 2/07 623/1.31 |
| 2008/0262595 A1 | 10/2008 | Chu et al. |
| 2009/0024072 A1 | 1/2009 | Criado et al. |
| 2009/0240316 A1 | 9/2009 | Bruszewski et al. |
| 2009/0287145 A1 | 11/2009 | Cragg et al. |
| 2011/0166644 A1 | 7/2011 | Keeble et al. |
| 2012/0197382 A1 | 8/2012 | Roeder et al. |
| 2013/0144373 A1 | 6/2013 | Shahriari et al. |
| 2013/0172984 A1 | 7/2013 | Greenberg et al. |
| 2014/0172064 A1 | 6/2014 | Kelly |
| 2014/0316513 A1 | 10/2014 | Tang et al. |
| 2015/0105850 A1 | 4/2015 | Shahriari |

OTHER PUBLICATIONS

International Search Report PCT/US2015/013344, dated May 6, 2015.
International Search Report PCT/US2016/024125, dated Jun. 17, 2016.

* cited by examiner

PARARENAL AND THORACIC ARCH STENT GRAFT AND METHODS FOR USE

CROSS REFERENCE TO RELATED APPLICATIONS

This application claims priority to and the benefit of U.S. Provisional Application No. 62/138,299, filed on Mar. 25, 2015 and U.S. Provisional Application No. 62/197,304, filed on Jul. 27, 2015, which are each hereby incorporated by reference in their entirety.

BACKGROUND

Unless otherwise indicated herein, the materials described in this section are not prior art to the claims in this application and are not admitted to be prior art by inclusion in this section.

Pararenal and juxtarenal aneurysms are infrarenal aneurysms located within about 5 mm of the renal arteries that have very short necks (i.e., less than 5 mm) or that involve 2-3 visceral arteries (e.g., right and left renal arteries and occasionally the superior mesenteric artery ("SMA")) and that extend to within about 5 mm of the SMA. Since a pararenal aneurysm typically includes only a portion of the visceral trunk of the aorta, obtaining a proximal seal between a main body stent graft and the vascular tissue is difficult since blood flow must be maintained to the renal arteries, the SMA and the celiac artery. One technique to treat a pararenal aneurysm may involve placing bridging stent grafts in each of the foregoing arteries via a branched or manifold stent graft, for example. While this technique may provide a sufficient proximal seal between the stent graft and the vasculature, the proximal seal may also create a new risk, namely that blood flow to the lumbar arteries may be blocked by the proximal seal. Specifically, the lumbar arteries perfuse the spinal cord with blood, and they tend to be concentrated in the area of the thoracic aorta above the celiac arteries in the "seal zone" for stent grafts placed and anchored in the aorta. As such, cutting off blood flow to the lumbar arteries may cause a patient to become hemodynamically unstable (i.e., blood pressure is too low to sufficiently perfuse tissues with blood) and may put a patient at risk for paraplegia. In addition, the Great vessels located in the aortic arch near the heart may similarly have blood flow cutoff by known treatment devices and methods for thoracic aneurysm and may lead to stroke.

SUMMARY

Example embodiments beneficially provide stent grafts for treating pararenal, supra-renal, ascending, transverse and descending thoracic aneurysms, for example, and methods for placing these stent grafts. The stent graft disclosed herein provides several advantages over known techniques. For example, the stent graft may permit a pararenal aneurysm to be repaired endovascularly with minimal coverage of the aorta above the celiac artery. This may be accomplished through an indentation or scallop-shaped-hole defined at the proximal end of the main body stent graft and arranged below the lumbar arteries upon deployment in vivo, while the remainder of the proximal end of the stent graft extends along the visceral trunk of the aorta. The proximal end of the main body stent graft may in turn be supported by a proximal sealing ring having a bi-level construction defining an upper portion arranged along the most proximal edge of the main body stent graft and a lower portion arranged along the indentation or scallop-shaped hole.

In addition, the stent graft may beneficially provide a diaphragm disposed within the main lumen that defines at least three openings. In one embodiment, these openings may include first, second, third and fourth openings. This arrangement may permit one or more bridging stents that may be coupled directly to these openings or to stent grafts coupled to these openings. This allows the exclusion of an aneurysm distal to the main body stent graft down through the iliac arteries, for example.

Further, in one embodiment, stent graft extensions may be coupled to the third and fourth openings of the diaphragm and may be arranged to cross-over one another with gentle swooping paths for stenting to the renal arteries. This configuration may advantageously permit unobstructed blood flow and may minimize both the potential for kinking of the stent grafts and for turbulent blood flow. Also, in a further embodiment, the third and fourth openings may be positioned on opposite sides of the diaphragm between the sidewall of the main body stent graft and the center of the lumen defined by the main body stent graft. This arrangement may provide for a gentle swooping path of the stent graft extensions coupled to the third and fourth openings, because free ends of the stent graft extensions may have more space to cross to the opposite side of the main body stent graft. In an alternative embodiment, the third and fourth openings may be positioned in the diaphragm closer to the center of the lumen defined by the main body stent graft. This arrangement may beneficially result in a higher blood flow rate.

In addition, in one embodiment, a permeable membrane may be provided covering at least one of a visceral vessel opening and two renal openings. This permeable membrane may advantageously increase contact area with the aortic wall upon deployment, while at the same time permitting blood flow across the membrane for a temporary period of time while the blood is inhibited from forming clots due to heparinization, for example. The permeable membrane may be perforable by a guidewire and/or a stent graft and any resistant force against the stent graft may be negligible. Once deployed in vivo, thrombosis may be formed on the permeable membrane thereby beneficially extending the seal zone of the stent graft with the aortic wall.

Also, in one embodiment, a visceral chamber may be defined by a visceral sidewall coupled to one of the diaphragm and the second opening and to one of the sidewall of the main body stent graft and the visceral-vessel opening defined in the sidewall of the main body stent graft. This visceral chamber may beneficially permit native blood flow to continue to the celiac and SMA arteries. In addition, in the event that an aneurysm advances proximally after placement of the stent graft, the aneurysm may be repaired by a standard thoracic stent graft that may be deployed and mate directly with the lumen of the main body stent graft.

With respect to thoracic aneurysm, the stent graft may provide blood flow to all three Great vessels thereby treating from the sinotubular junction and providing unimpeded flow during debranching of the aneurysm. The stent graft may also advantageously provide a surgeon with the flexibility to choose between placing the arch bypass graft or debranching the Great vessels first. For example, it may be desirable to debranch the Great vessels first and thereby provide stroke protection during subsequent placement of the larger arch bypass graft. Thus, the stent graft allows the surgeon to elect between risks based upon the presentation of each individual patient.

Thus, in one aspect, a stent graft is provided including the features of (a) a main body stent graft defining a lumen having a first end and a second end, (b) a diaphragm coupled to the main body stent graft, where the diaphragm defines at least three openings, and (c) at least three stent graft extensions each defining a lumen, where a first end of each of the at least three stent graft extensions is coupled to one of the at least three openings.

In a second aspect, the stent graft includes the features of (d) a visceral-vessel opening defined in a sidewall of the main body stent graft between the first end and the second end of the main body stent graft, where the diaphragm is disposed within the lumen of the main body stent graft, where the at least three openings of the diaphragm comprise a first opening, a second opening, a third opening and a fourth opening, and (e) a visceral chamber defined by a sidewall coupled to one of the second opening and the diaphragm and to one of the visceral-vessel opening and the sidewall of the main body stent graft.

In a third aspect, a stent graft includes the features of (a) a visceral-vessel opening defined in a sidewall of the main body stent graft between the first end and the second end of the main body stent graft, where the diaphragm is disposed within the lumen of the main body stent graft, and where the at least three openings of the diaphragm comprise a first opening, a second opening, a third opening and a fourth opening.

In a fourth aspect, a method for placement of the stent graft is provided including the steps of (a) introducing a guidewire into any appropriately sized arterial configuration via arterial access, (b) loading a delivery catheter containing the stent graft according to the first aspect onto the guidewire, (c) moving the delivery catheter along the guidewire and introducing the delivery catheter into the appropriately sized arterial configuration via arterial access, and (d) deploying the stent graft into the appropriately sized arterial configuration and/or a lumen of a previously-placed stent graft.

In a fifth aspect, a stent graft includes the features of (a) a main body stent graft defining a lumen having a first end and a second end, (b) a diaphragm coupled to the main body stent graft, where the diaphragm defines a first opening, a second opening and a third opening;, (c) a first stent graft extension having a first end and a second end, where the first stent graft extension has a single lumen, where the first end of the first stent graft extension is coupled to the diaphragm and arranged surrounding the first opening, (d) a second stent graft extension having a first end and a second end, where the second stent graft extension has a single lumen at the first end and has a bifurcation defining two lumens at the second end, where the first end of the second stent graft extension is coupled to the diaphragm and arranged surrounding the second opening and (e) a third stent graft extension having a first end and a second end, where the third stent graft extension has a single lumen at the first end and where the first end of the third stent graft extension is coupled to the diaphragm and arranged surrounding the third opening.

In a sixth aspect, a stent graft includes the features of (a) a main body stent graft that defines a lumen with first and second ends, (b) a diaphragm coupled to the main body stent graft within the lumen, where the diaphragm defines at least three openings, (c) at least three stent graft extensions each defining a lumen, where a first end of each of the at least three stent graft extensions is coupled to one of the at least three openings, (d) a visceral vessel opening defined in the sidewall of the main body stent graft, (e) two renal openings defined in the sidewall of the main body stent graft distal to the diaphragm and (f) permeable membrane material covering at least one of the visceral vessel opening and the two renal openings.

These as well as other aspects, advantages, and alternatives, will become apparent to those of ordinary skill in the art by reading the following detailed description, with reference where appropriate to the accompanying drawings.

DETAILED DESCRIPTION

Figure 1:
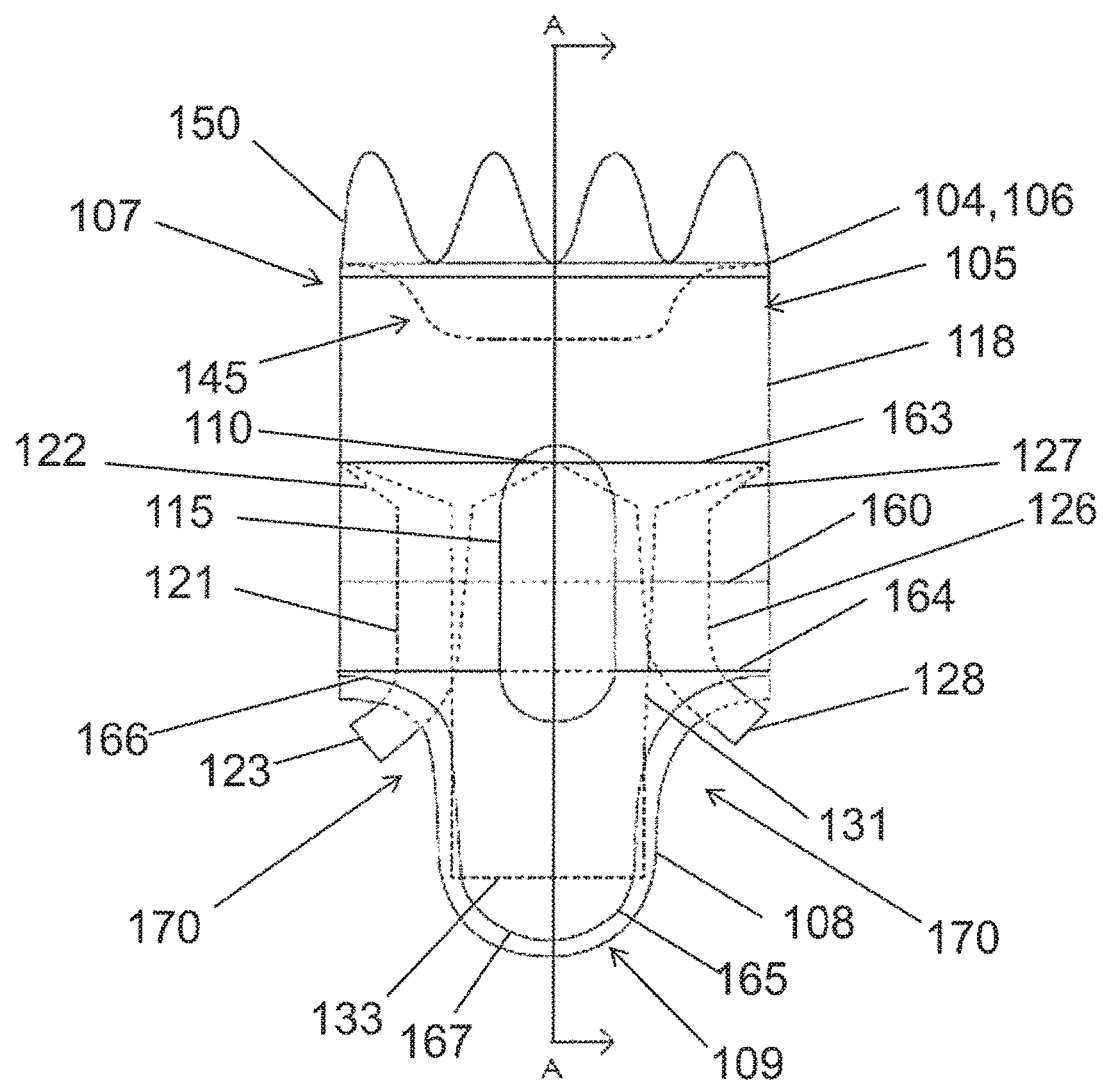
FIG. 1 is a front view of the stent graft according to one example embodiment.
Figure 2:
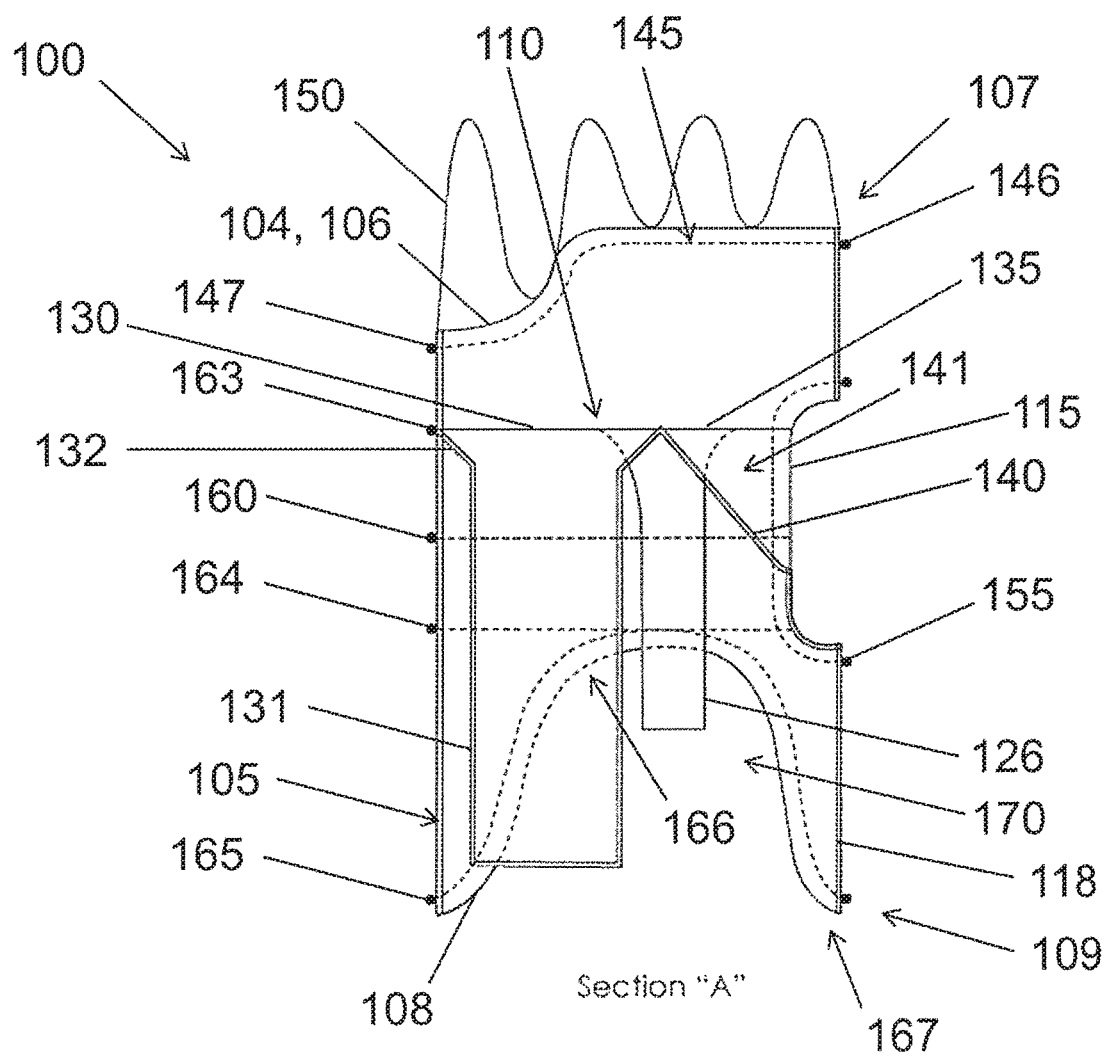
FIG. 2 is a cross-sectional side view of Section A:A from FIG. 1.
Figure 3:
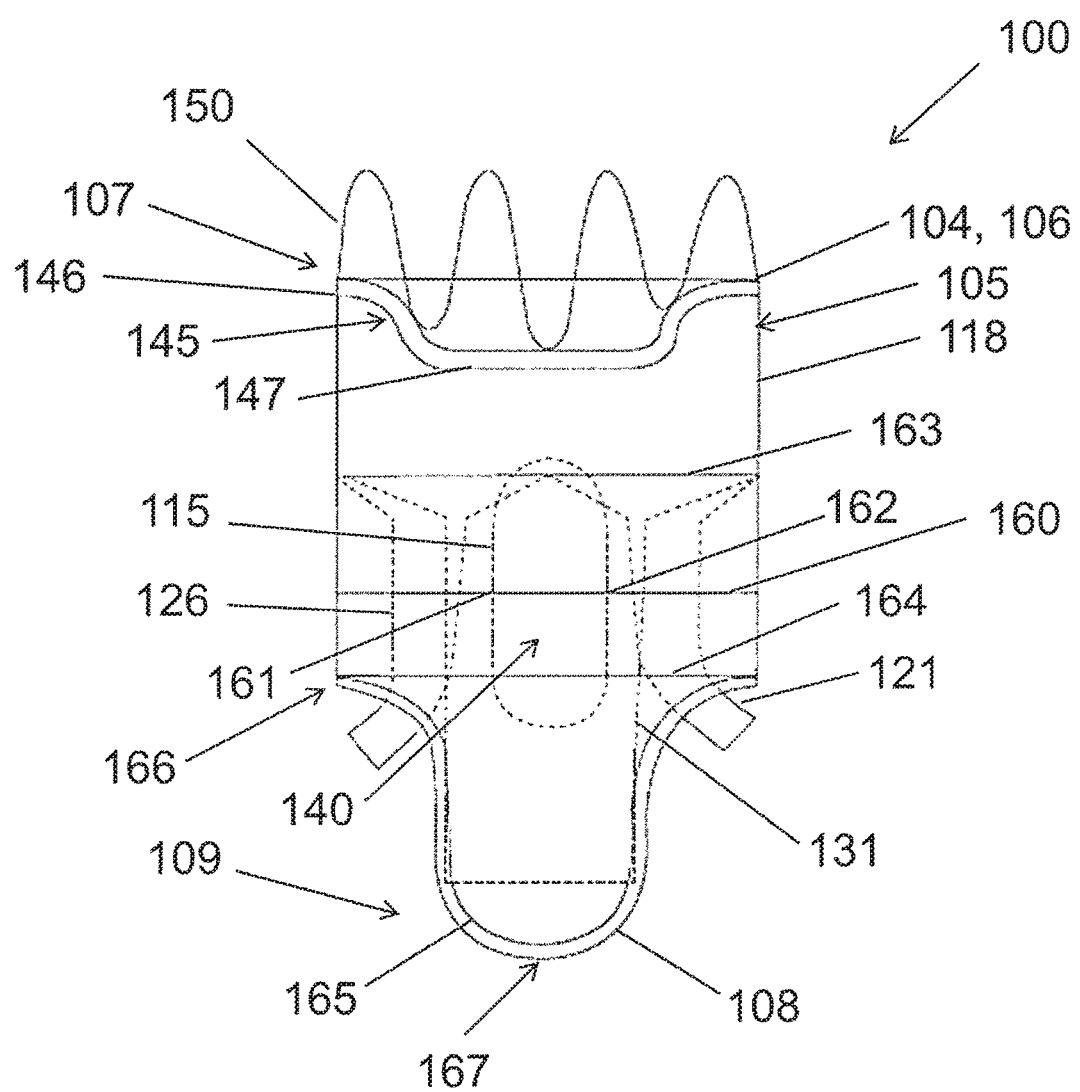
FIG. 3 is a back view of the stent graft according to the example embodiment of FIG. 1.
Figure 4:
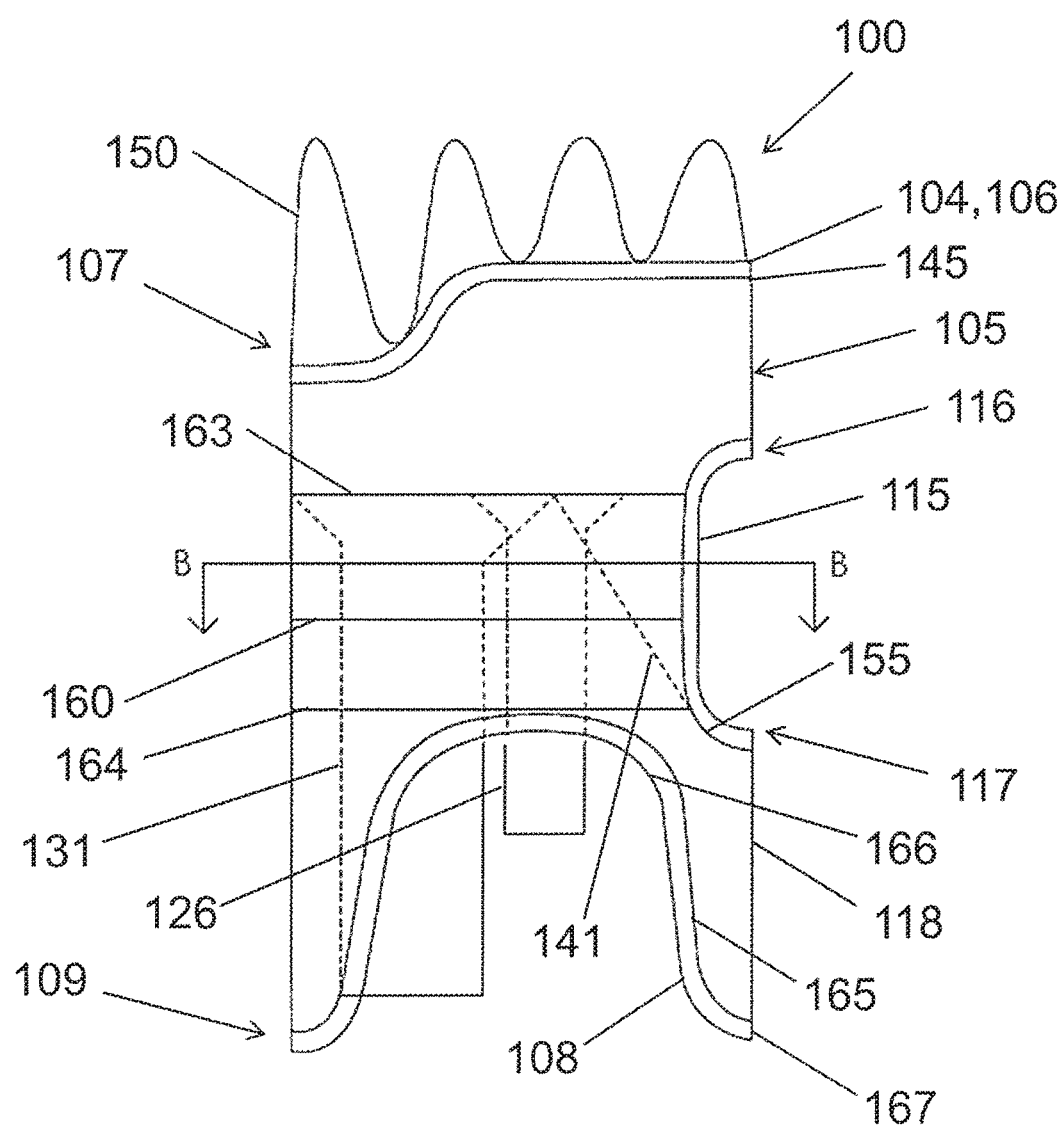
FIG. 4 is a side view of the stent graft according to the example embodiment of FIG. 1.
Figure 5:
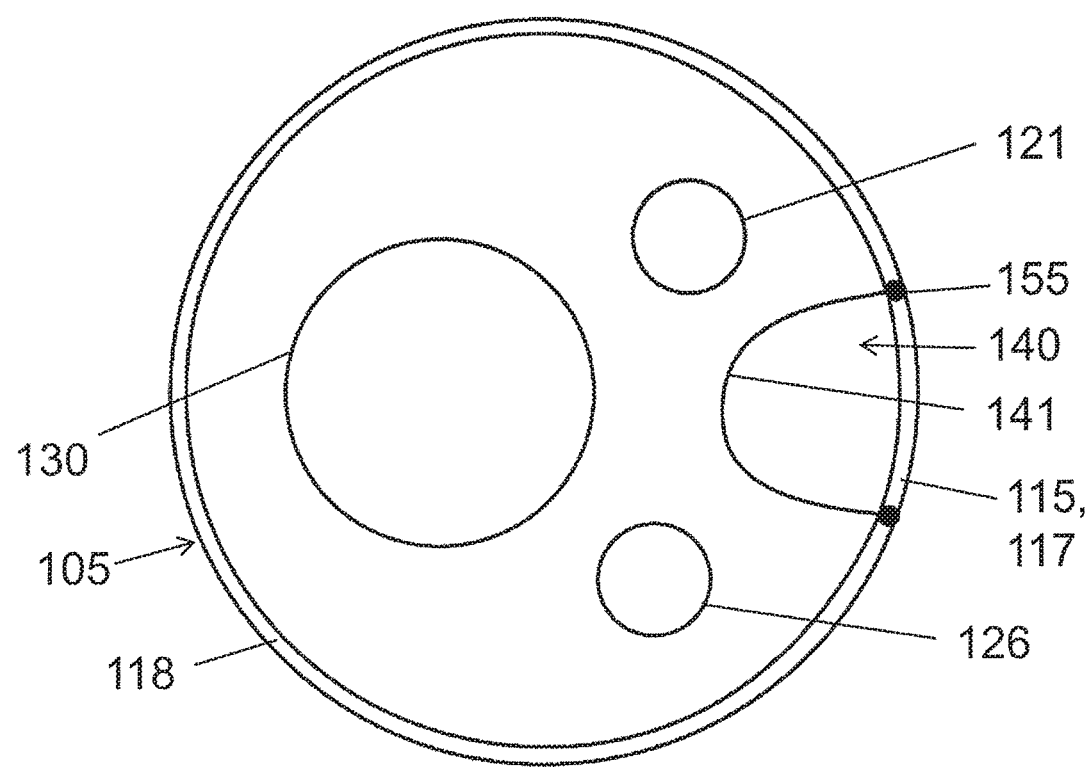
FIG. 5 is a cross-sectional top view of Section B:B from FIG. 4.

Example stent grafts, as well as methods of placement of the stent grafts, are described herein. Any example embodiment or feature described herein is not necessarily to be construed as preferred or advantageous over other embodiments or features. The example embodiments described herein are not meant to be limiting. It will be readily understood that certain aspects of the disclosed methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, "about" means +/−5%.

As used herein, diameter ranges pertain to an unconstrained, ex vivo state of the stent graft and stent graft extensions. When the stent graft and stent graft extensions are in a deployed, in vivo state the diameter ranges will be on the order of about 10-20% smaller in diameter than the ex vivo state.

As used herein, "pararenal" means a region adjacent to the kidney.

As used herein, "infrarenal" means situated or occurring below the kidneys.

As used herein, "visceral trunk" refers to the portion of the aorta attached to the renal arteries, superior mesenteric artery ("SMA"), and the celiac artery.

As used herein, "proximal end" refers to the end of the main body stent graft that will be positioned closer to a patient's heart than the "distal end" upon deployment.

As used herein, a "sealing ring" is a structure configured to apply an outward circumferential force to create a fluid tight seal. In some embodiments, this circumferential force may be applied laterally against the sidewall of the main body stent graft. In other embodiments, the circumferential force may be applied to maintain a hole or opening in a sidewall of the main body stent graft both in an open condition and in contact with vasculature. A sealing ring may be circular or oval, may be continuous or discontinuous, and/or may be contoured or have a bi-level shape to accommodate indentations or scallop-shaped holes in the sidewall of the main body stent graft, among other possibilities. The sealing rings may include elastic recoil material, such as nitinol, a standard stent structure or a straight reinforced wire, an injectable sealing agent that may form a sealing structure similar to a gasket or "O" ring among other possibilities.

As used herein, "passive fixation" refers to friction, interaction between the cloth of the grafts, radial strength of the stent structure and blood pressure that holds the component stent grafts together at the site of overlap.

As used herein, "active fixation" refers to features coupled to a stent, graft, or stent graft that may actively engage vasculature or another stent graft, including hooks, bi-directional hooks, stent structure elements, anchors, staples, bio-activated adhesive, or a combination thereof, among other possibilities.

As used herein, "string" refers to a low friction material such as GORE-TEX® Suture, for example.

As used herein, with respect to measurements, "about" means +/−5%.

As used herein, a "stent graft" is a tubular, radially-expandable device comprising a fluid-tight (i.e., blood-tight) fabric supported by a stent and may be used to bridge diseased arteries. Such stent grafts and methods for their deployment and use are known to those of skill in the art. For example, vascular sheaths can be introduced into the patient's arteries, through which items, including but not limited to, guidewires, catheters and, eventually, the stent graft, are passed.

As used herein, "stent" is typically a cylindrical frame and means any device or structure that adds rigidity, expansion force, or support to a prosthesis or native vasculature, while "stent graft" refers to a prosthesis comprising a stent and a graft material associated therewith that forms a fluid-tight lumen through at least a portion of its length. As used herein, "fluid tight" means a barrier that is configured to prevent or, upon deployment in vivo, becomes able to prevent blood or blood products (i.e. serum and its contents) from passing through, thus preventing an endoleak. For example, the stent structure may comprise coiled, mesh, zig-zag or woven wires or a laser cut tube. A "graft" is a substantially cylindrical liner or a non-linear graft in a tapered configuration that may be disposed on the stent's interior, exterior or both. In some embodiments, grafts may be woven as unitary structures with multiple lumens. For example, the main body stent graft, the diaphragm, the two renal lumens, the infrarenal lumen and the visceral chamber may all be woven together as a unitary structure or otherwise joined together to form a unitary structure. Further, when used in combination with a graft, the stent structure may further comprise a series of spaced apart stent rings disposed along the graft. A wide variety of attachment mechanisms are available to join the stent and graft together, including but not limited to, sutures, adhesive bonding, heat welding, and ultrasonic welding.

The stent can be made of any suitable material, including but not limited to biocompatible metals, implantable quality stainless steel wires, nickel and titanium alloys, and bio-compatible plastics attached to a graft. Any suitable fluid tight (i.e., blood-tight) graft material can be used. In a preferred embodiment, the graft material is a biocompatible fabric, including but not limited to woven or knitted polyester, such as poly(ethylene terephthalate), polylactide, polyglycolide and copolymers thereof; fluorinated polymers, such as PTFE, expanded or electrospun PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages, woven nickel-titanium and polyurethanes containing siloxane segments. Materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. The graft material may also include extracellular matrix materials.

The covered stent grafts can be made of any suitable material, including but not limited topolytetrafluoroethylene (ePTFE) lined nickel-titanium alloy stent. The stent grafts are preferably covered and flexible. The stent grafts may contain any other suitable components, such as surface modifications including but not limited to covalent attachment of heparin.

In a first aspect, shown in FIGS. 9-16, the invention provides a stent graft, comprising:
 a main body stent graft defining a lumen having a first end and a second end;
 a diaphragm coupled to the main body stent graft, wherein the diaphragm defines at least three openings; and
 at least three stent graft extensions each defining a lumen, wherein a first end of each of the at least three stent graft extensions is coupled to one of the at least three openings.

Referring now to FIGS. 9-16, a stent graft 200 is shown including a main body stent graft 205 defining a lumen that has a first end 207 and a second end 209. In one embodiment, the first end 207 of the main body stent graft 205 may be the proximal end of the stent graft 200 configured to be positioned closer to a patient's heart than the second end 209 or distal end of the main body stent graft 205 upon deployment. The diaphragm 210 may be coupled to the main body stent graft 205 at a location within the lumen or at the first end 207 or the second end 209. In one embodiment, the diaphragm 210 may be coupled to the main body stent graft 205 at a location ranging from the second or distal end 209 of the main body stent graft 205 up to a midsection of the main body stent graft 205. This arrangement may beneficially permit pressure from blood flow to act upon the proximal sidewall of the main body stent graft above the diaphragm, which may aid in sealing and fixation of the stent graft to the lumen in which it is deployed.

The diaphragm 210 defines at least three openings. For example, in one embodiment, the diaphragm 210 may define a first opening 230 coupled to a first stent graft extension 231, a second opening 235 coupled to a second stent graft extension 236, a third opening 220 coupled to a third stent graft extension 221 and a fourth opening 225 coupled to a fourth stent graft extension 226. In various embodiments, the first opening 230 may be used to receive a bridging stent for placement in the infrarenal segment of the aorta or other native vessel, the second opening 235 may be used to receive a bridging stent for placement in the celiac and SMA or other native vessel, the third and fourth openings 220, 225 may be used to receive a bridging stent for placement in the renal arteries or other native vessel. Alternatively, the first opening 230 may be used to receive a bridging stent for placement in the aortic arch, the second opening 235 may be used to receive a bridging stent for placement in the innominate (right common carotid artery and the right subclavian artery) or other native vessel, the third and fourth openings 220, 225 may be used to receive a bridging stent for placement in the left common carotid artery and the left subclavian artery or other native vessel.

Figure 11:
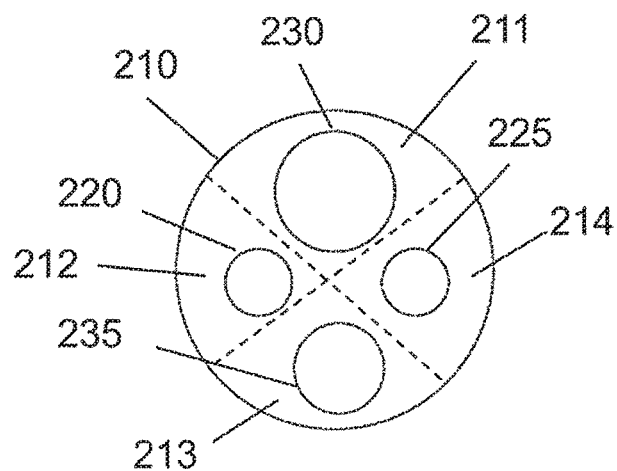
FIG. 11 is a top view of the stent graft according to a fourth example embodiment.
Figure 12:
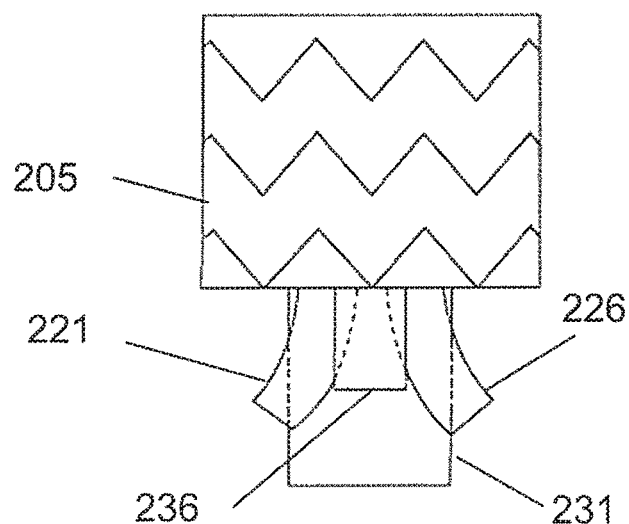
FIG. 12 is a front view of the stent graft according to the example embodiment of FIG. 11.

In one embodiment, shown in FIG. 11, the first opening 230 may have a diameter larger than a diameter of the second opening 235. In another embodiment, shown in FIG. 11, the diameter of the second opening 235 may be larger than a diameter of the third opening 220 and a diameter of the fourth opening 225. In an alternative embodiment, shown in FIGS. 9 and 14, the second opening 235, the third opening 220 and the fourth opening 225 may each have the same size diameter. In yet another embodiment shown in FIG. 11, the first opening 230 and the second opening 235 may be defined on opposite sides of the diaphragm 210. In a still further embodiment, the first opening 230, the second opening 235, the third opening 220 and the fourth opening 225 may each be defined in different quadrants 211-214 of the diaphragm 210, as shown in FIG. 11.

Figure 9:
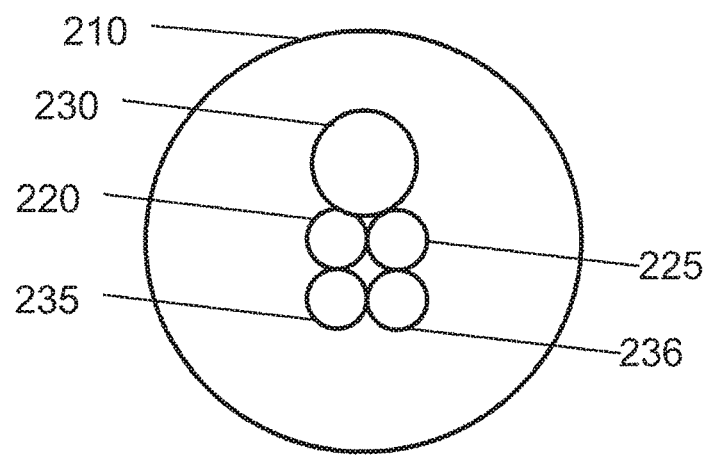
FIG. 9 is a top view of the stent graft according to a third example embodiment.
Figure 14:
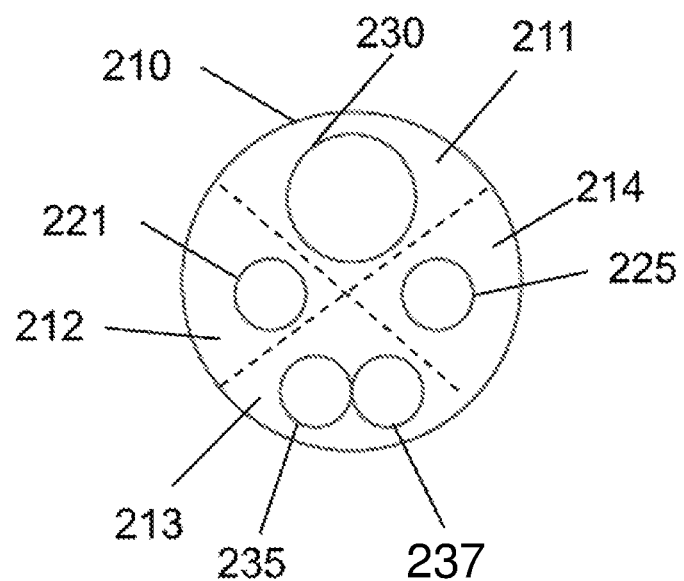
FIG. 14 is a top view of the stent graft according to a fifth example embodiment.
Figure 15:
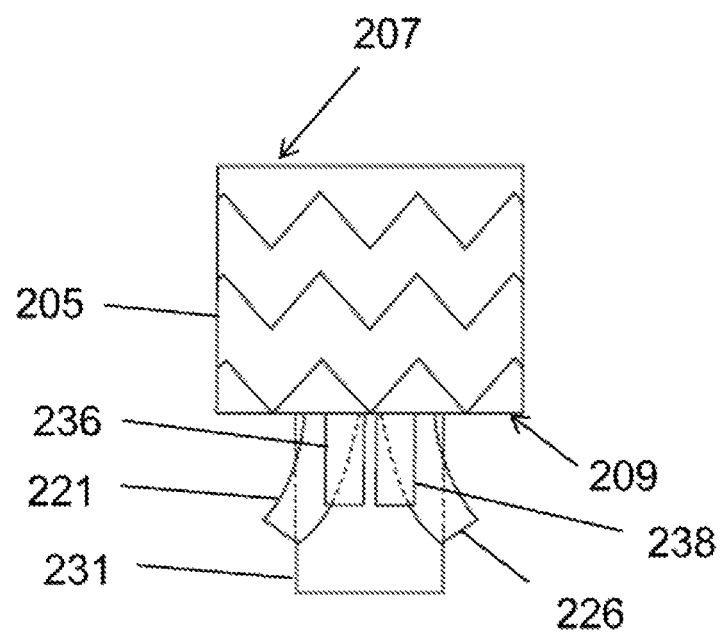
FIG. 15 is a front view of the stent graft according to the example embodiment of FIG. 14.
Figure 16:
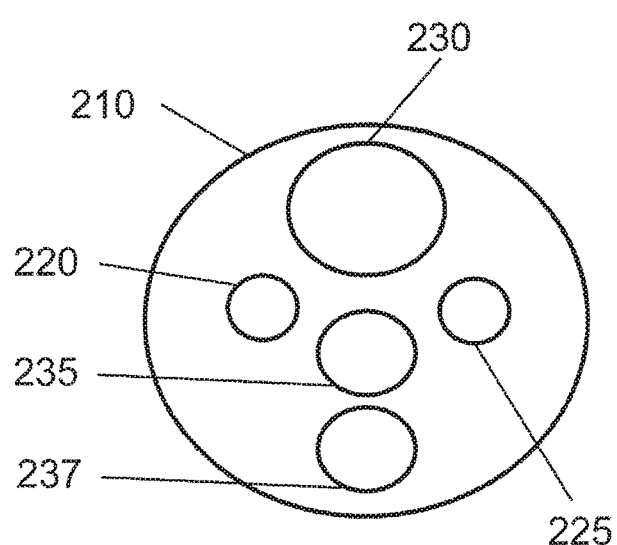
FIG. 16 is a top view of the stent graft according to a sixth example embodiment.
Figure 17:
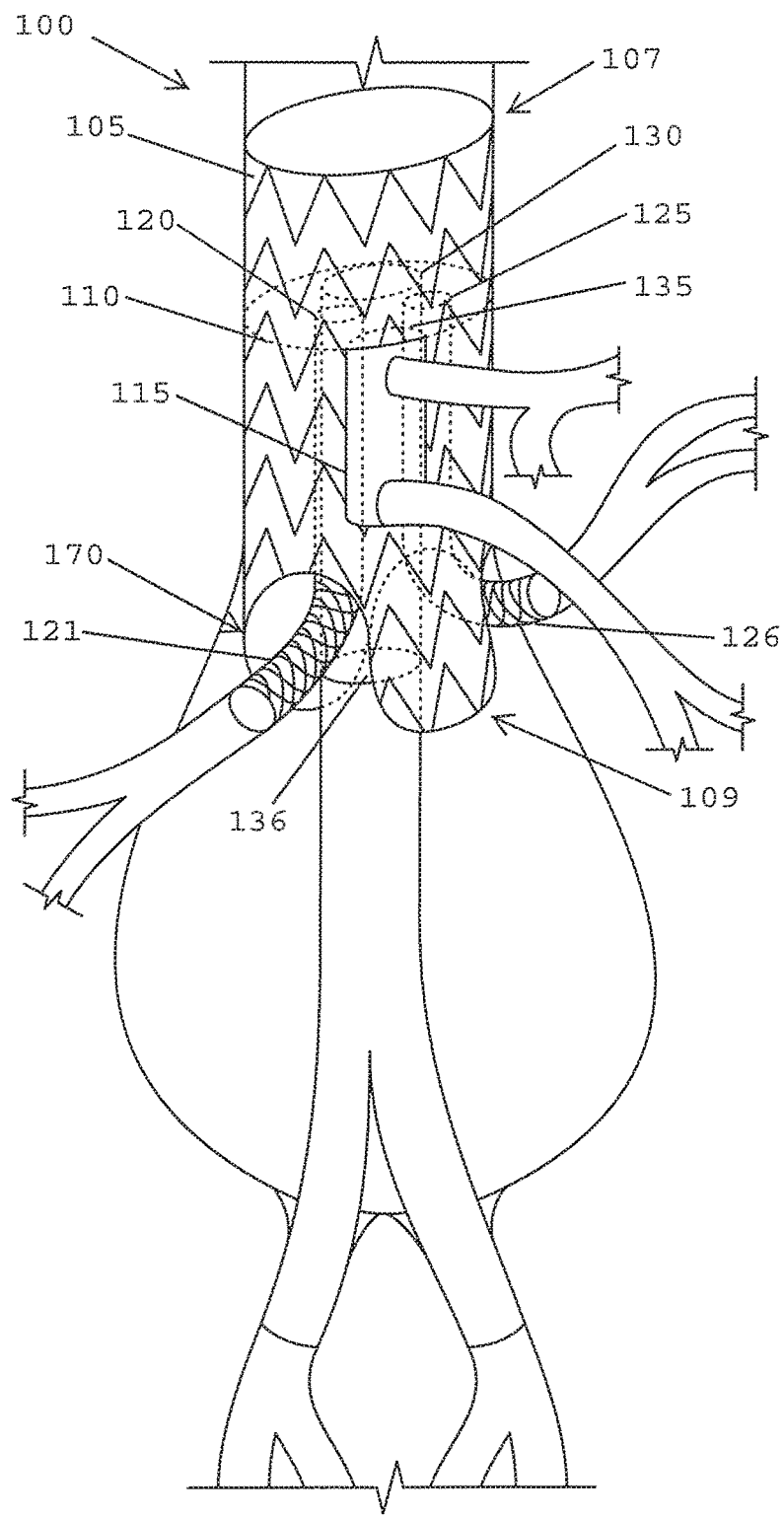
FIG. 17 is a cross-sectional front view of the abdominal aorta with a perspective view of the stent graft according to the example embodiment of FIG. 1 in an expanded condition.
Figure 18:
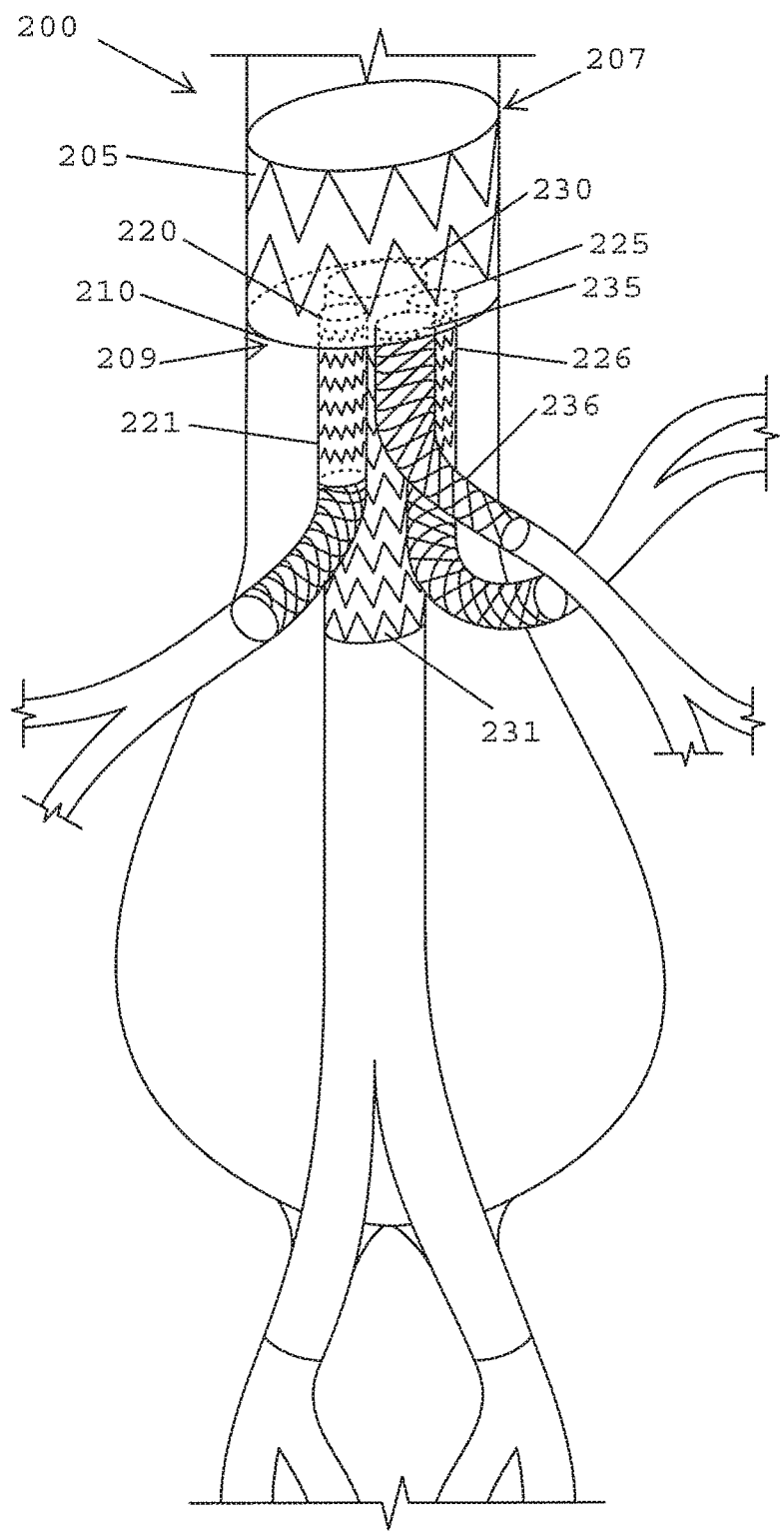
FIG. 18 is a cross-sectional front view of the abdominal aorta with a perspective view of the stent graft according to the example embodiment of FIG. 11 in an expanded condition.

In further embodiments shown in FIGS. 9, 14 and 16, a fifth opening 237 may also be defined in the diaphragm 210 and coupled to a fifth stent graft extension 238. In one embodiment, the fifth opening 237 may be used to receive a bridging stent for placement in the celiac and SMA or other native vessel. In one embodiment, the first opening 230 may have a diameter larger than a diameter of the second opening 235 and a diameter of the fifth opening 237 (see FIGS. 9, 14 and 16). In a further embodiment shown in FIG. 16, the diameter of the second opening 235 and the diameter of the fifth opening 237 may be larger than a diameter of the third opening 220 and a diameter of the fourth opening 225. In alternative embodiments, as shown in FIGS. 9 and 14, the diameter of the second opening 235 and the diameter of the fifth opening 237 may have the same dimension as a diameter of the third opening 220 and a diameter of the fourth opening 225. In one embodiment, the first opening 230, the second opening 235 and the fifth opening 237 may be arranged linearly in the diaphragm 210, and the third opening 220 and the fourth opening 225 may be arranged on opposite sides of each of the first, second and fifth openings 230, 235, 237, as shown in FIG. 16. In addition, as shown in FIG. 9, the third opening 220 and the fourth opening 225 may be arranged adjacent to each other and may be arranged together on a side of the diaphragm 210 opposite to the first opening 230. Still further, in one embodiment, the first opening 230 may be arranged in a first quadrant 211 of the diaphragm 210, the third opening 220 may be arranged in a second quadrant 212 of the diaphragm, the second opening 235 and the fifth opening 237 may be arranged in a third quadrant 213 of the diaphragm and the fourth opening 225 may be arranged in a fourth quadrant 214 of the diaphragm 210, as shown in FIG. 14.

Figure 10:
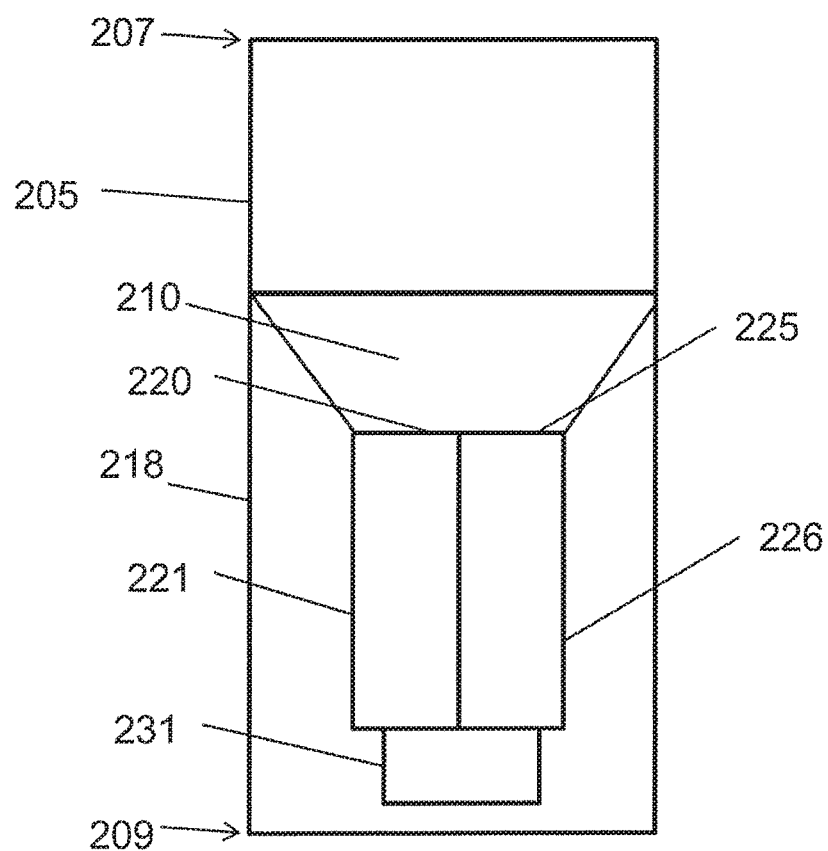
FIG. 10 is a side cross-sectional view of the stent graft according to the example embodiment of FIG. 9.

In yet another embodiment, at least a portion of the diaphragm 210 may be angled relative to a sidewall 218 of the main body stent graft 205 toward the second end 209 of the main body stent graft 205. In one embodiment, as shown in FIGS. 9-10, the openings 220, 225, 230 in the diaphragm 210 may be defined in the center of the diaphragm 210, and the diaphragm 210 may be substantially funnel-shaped. In a further embodiment, an end of at least one of the stent graft extensions may be tapered adjacent to the diaphragm 210, as shown and described with respect to the first aspect of the invention. This arrangement may aid with guidewire alignment and entry into the respective lumens of the stent graft extensions in order to place extension or bridging stents and may encourage laminar blood flow.

In addition, in one embodiment, the openings of the diaphragm 210 may be reinforced to mate with bridging stent grafts or extension stent grafts, for example. The reinforcement material may include nitinol, for example, or any nonextendible, collapsible material that is biocompatible. In a further embodiment, the diaphragm 210 may have an expandable frame that may be configured to apply an outward radial force to the main body stent graft 205, as discussed with respect to the first aspect of the invention. This frame may aid with fixation and seal with a vessel lumen.

In one embodiment, the diameter of the main body stent graft 205 may range from about 20 mm to about 65 mm, and preferably in the visceral segment from about 23 mm to about 40 mm or from about 28 mm to about 36 mm and preferably in the thoracic aorta from about 30 mm to about 65 mm or from about 40 mm to about 55 mm. In addition, the length of the main body stent graft 205 may range from about 10 mm to about 150 mm and preferably from about 20 mm to about 60 mm. Further, each of the second stent graft extension 236 and the fifth stent graft extension 238 may have a length ranging from about 0.5 mm to about 40 mm, in on example. In yet another embodiment, each of a diameter of the second stent graft extension 236 and a diameter of the fifth stent graft extension 238 may range from about 6 mm to about 14 mm.

In one embodiment, the first stent graft extension 231 may have a length of at least 30 mm and may have a diameter ranging from about 8 mm to about 25 mm. In another embodiment, the first opening 230 may have a diameter ranging from about 8 mm to about 25 mm. In a further embodiment the third opening 220 and the fourth opening 225 may each have a diameter ranging from about 4 mm to about 25 mm. In another embodiment, the third stent graft extension 221 and the fourth stent graft extension 226 may each have a diameter ranging from about 4 mm to about 12 mm.

The stent graft 200 may also include a plurality of sealing rings coupled to the main body stent graft 205, as discussed above with respect to the first aspect of the invention. For example, in one embodiment, the plurality of sealing rings may include a proximal sealing ring 245 coupled to the main body stent graft 205 at or directly adjacent to the first end 207. In one embodiment, the proximal sealing ring 245 may have a bi-level construction defining an upper portion and a lower portion. In an alternative embodiment, the proximal sealing ring may be ring-shaped.

Figure 13A:
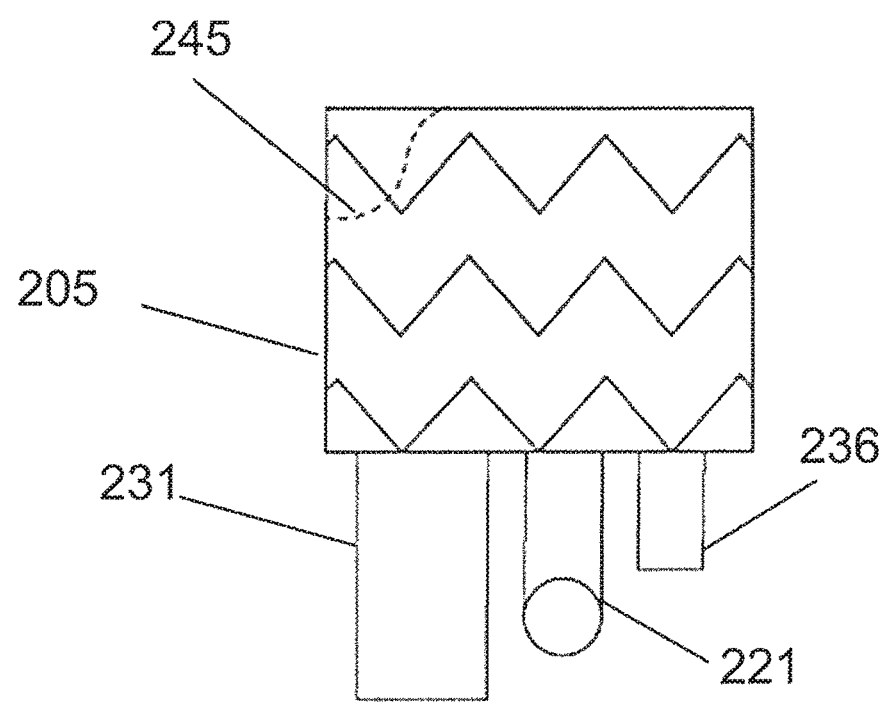
FIG. 13A is a side view of the stent graft according to the example embodiment of FIG. 11.
Figure 13B:
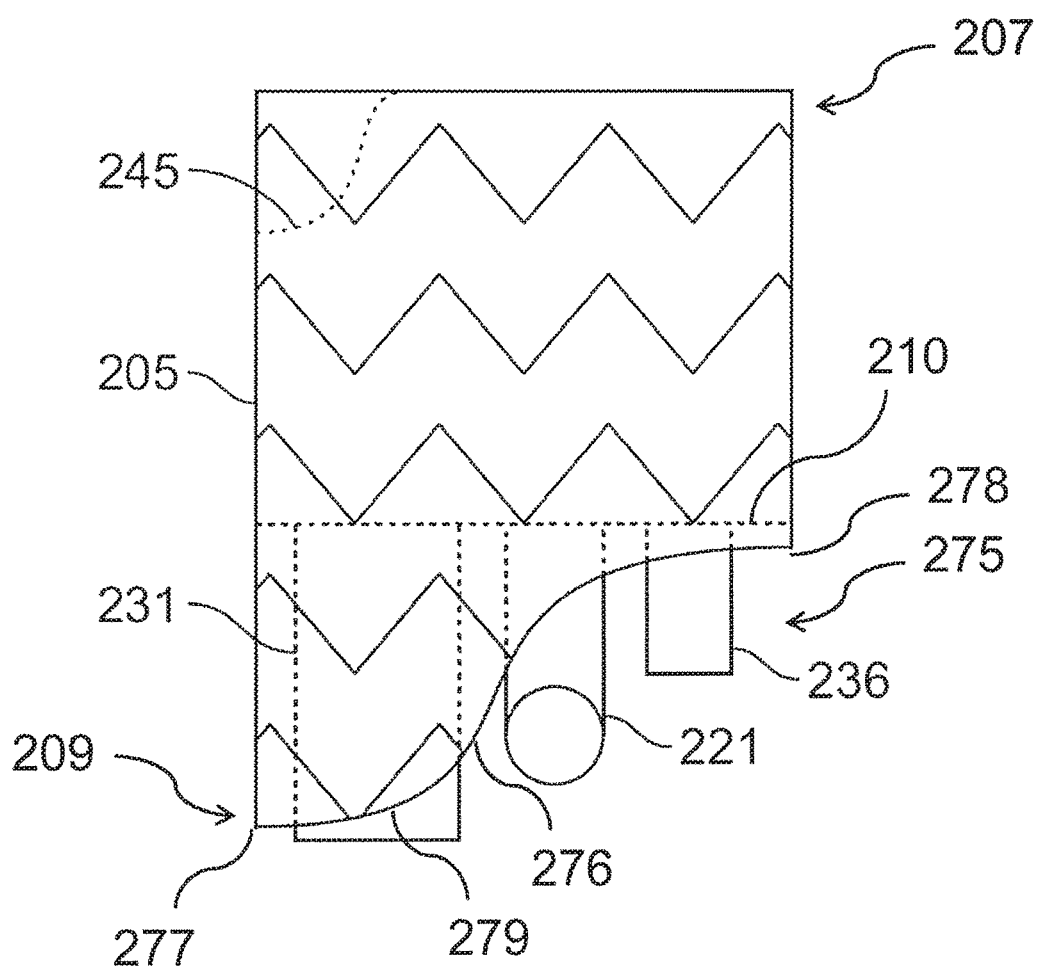
FIG. 13B is a side view of the stent graft according to the example embodiment of FIG. 11 further including a visceral vessel opening having an inverted U-shape defined in the sidewall of the main body stent graft.
Figure 23:
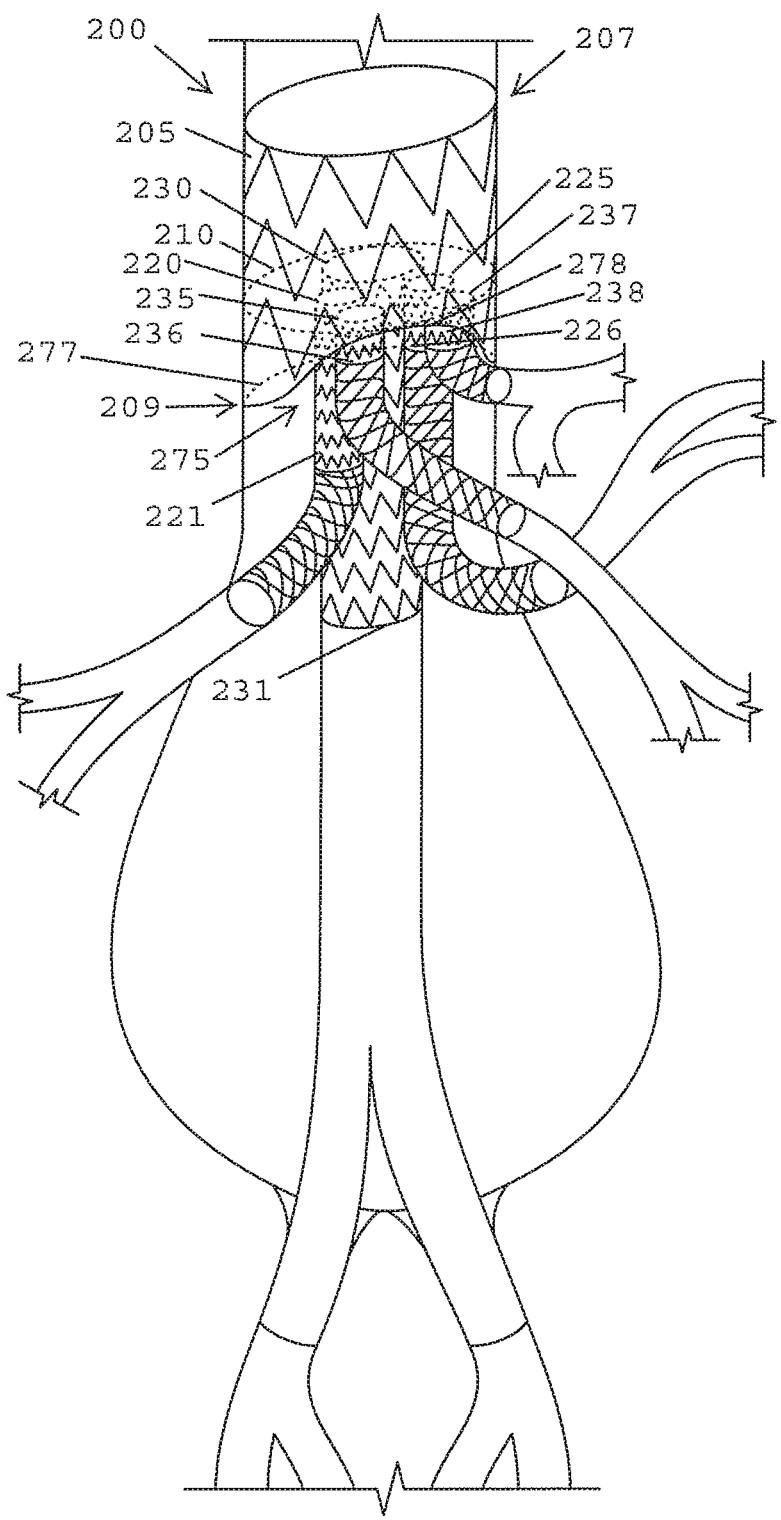
FIG. 23 is a cross-sectional front view of the abdominal aorta with a perspective view of the stent graft according to the example embodiment of FIG. 13B in an expanded condition.

In one embodiment, shown in FIGS. 13B and 23, the stent graft may include a visceral vessel opening 275 having an inverted U-shape defined in the sidewall of the main body stent graft 205 and extending from the diaphragm 210 to the second end 209 of the main body stent graft 205. The visceral opening may advantageously avoid blocking blood flow and permit access to the celiac and SMA arteries. In a further embodiment, the plurality of sealing rings may include a distal sealing ring 176 coupled to the main body stent graft 205 between the diaphragm 210 and the second end 209 of the main body stent graft 205. The distal sealing ring 276 may have a radial portion 277 arranged about a portion of the circumference of the main body stent graft 205 and an arch portion 278 aligned with the visceral vessel opening 275. In one embodiment, each end of the radial portion 277 of the distal sealing ring 276 may transition to the arch portion 278 via two curved segments 279 each having a radius of curvature ranging from about 20 mm to about 50 mm. In still another embodiment, the length of the main body stent graft 205 between the first end 207 and the diaphragm 210 may range from about 10 mm to about 150 mm. In a further embodiment, the length of the main body stent graft 205 from the diaphragm 210 to the second end 209 of the main body stent graft 205 may range from about 0.05 mm to about 40 mm.

In another embodiment, as discussed below with respect to the second aspect of the invention, a pair of opposing helical stent structures may be coupled to one or more of the first stent graft extension 231, the second stent graft extension 236, the third stent graft extension 221, the fourth stent graft extension 226 and the fifth stent graft extension 238.

In still another embodiment, the first end 207 of the main body stent graft 205 may be coupled to a fixation stent, as described below with respect to the second aspect of the invention.

Figure 19:
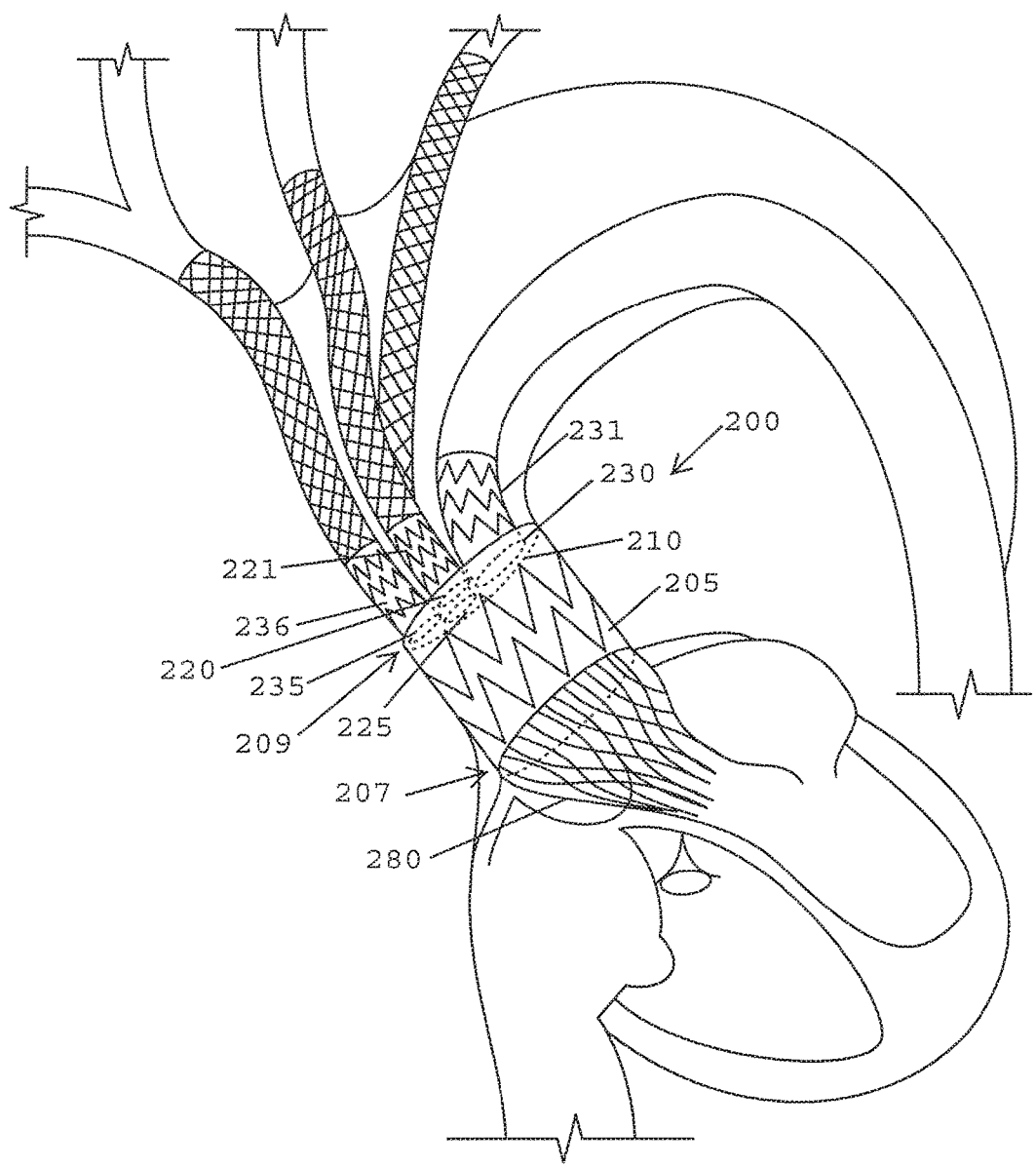
FIG. 19 is a cross-sectional front view of the aortic arch with a perspective view of the stent graft according to the example embodiment of FIG. 11 in an expanded condition.
Figure 20:
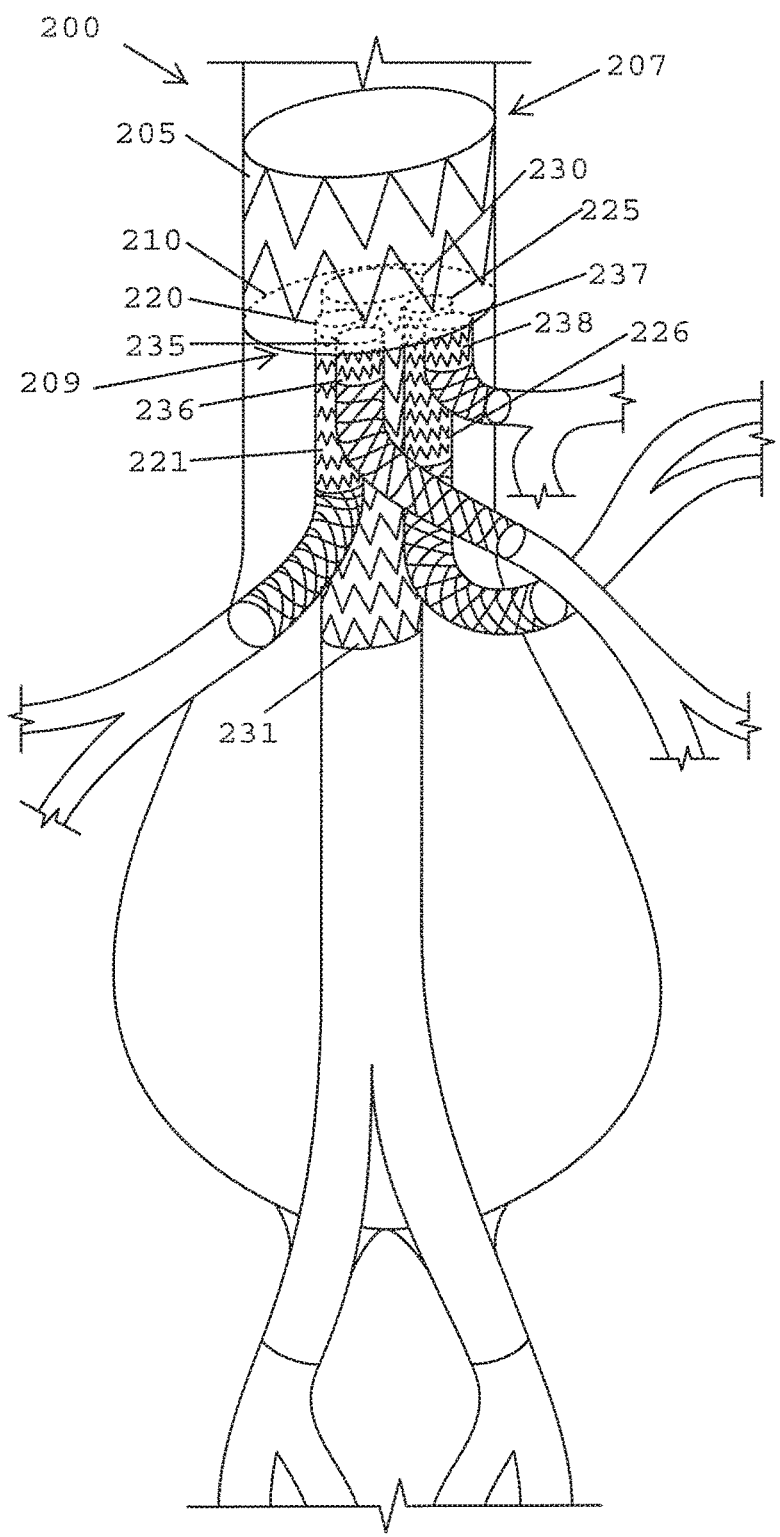
FIG. 20 is a cross-sectional front view of the abdominal aorta with a perspective view of the stent graft according to the example embodiment of FIG. 14 in an expanded condition.
Figure 21:
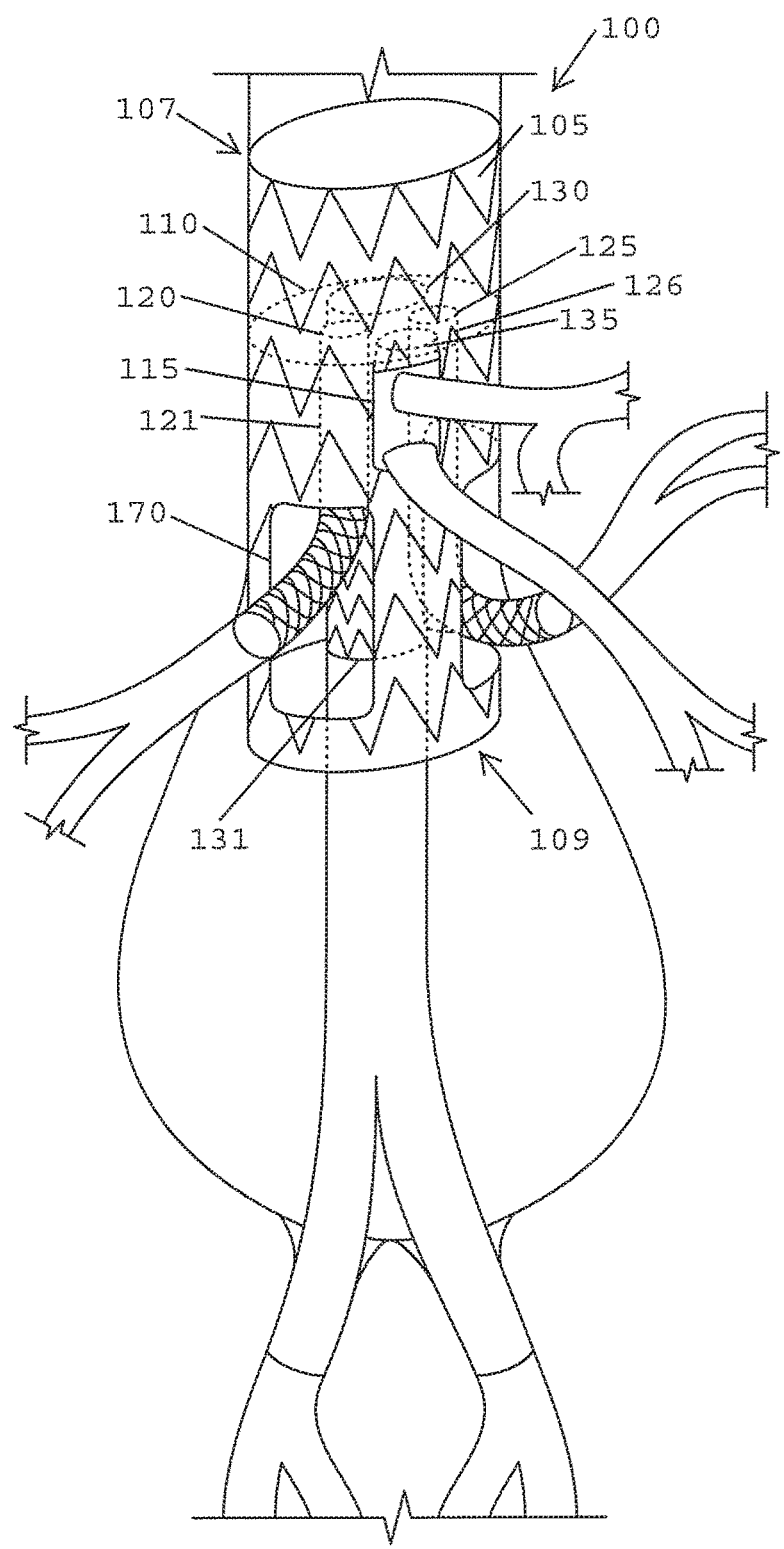
FIG. 21 is a cross-sectional front view of the abdominal aorta with a perspective view of the stent graft according to the example embodiment of FIG. 7 in an expanded condition.
Figure 22:
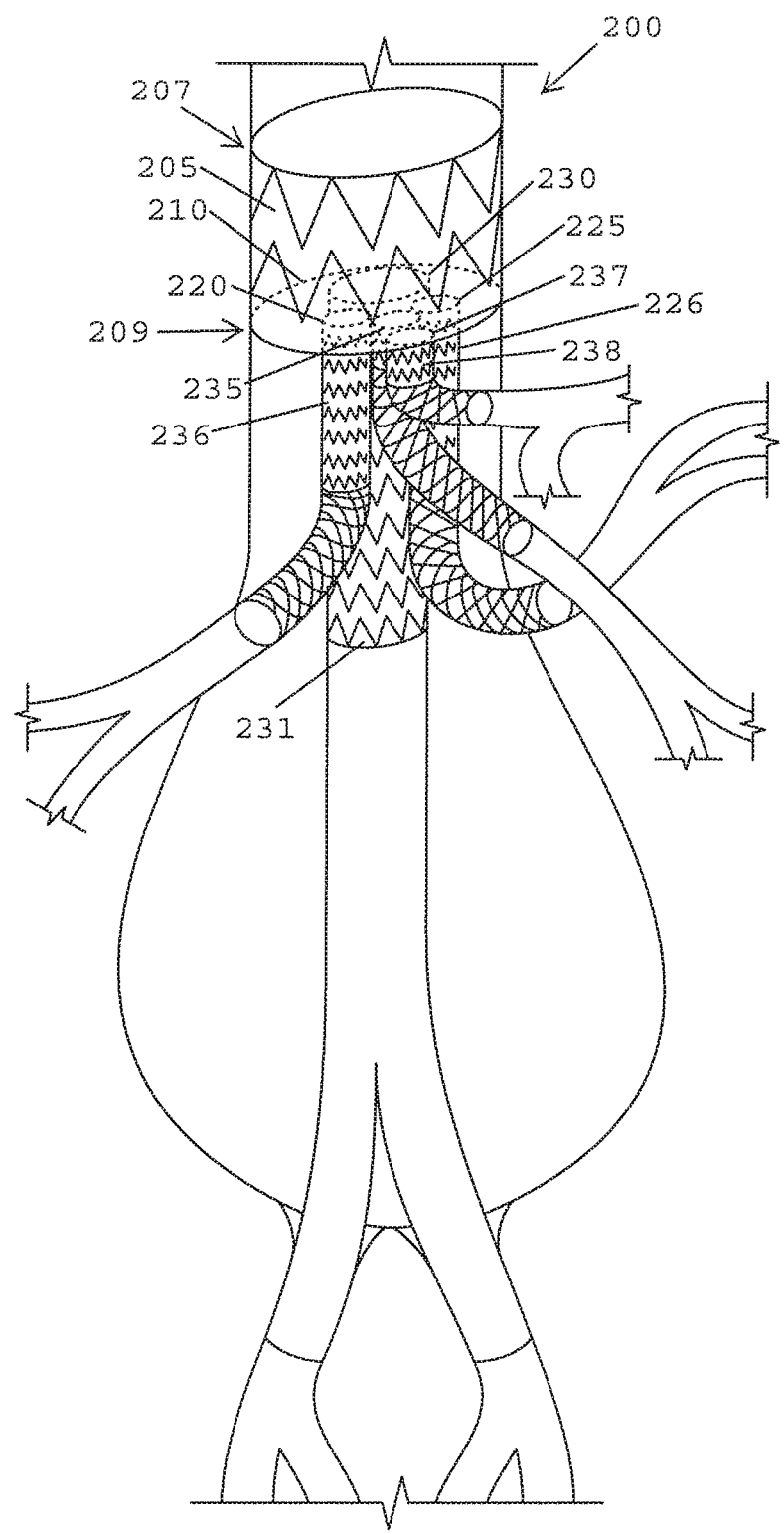
FIG. 22 is a cross-sectional front view of the abdominal aorta with a perspective view of the stent graft according to the example embodiment of FIG. 16 in an expanded condition.

In an alternative embodiment, shown in FIG. 19, the stent graft may include a stent valve 280 affixed to the first end 207 of the main body stent graft 205. In this arrangement, a free end of the stent valve may be covered and a portion of the stent valve extending between the free end and the main body stent graft 205 may be uncovered. As used herein, a "stent valve" is a percutaneous self-expanding valve affixed to a proximal or first end 207 of the main body stent graft 205 with the uncovered portion overlaying the coronary arteries to maintain blood flow. An exemplary embodiment of the stent valve includes the Corevalve® manufactured by Medtronic. In one embodiment, the free end of the stent valve may be covered with an impervious natural or synthetic material. In one embodiment, the stent valve may be placed in the outflow tract of the aortic valve. The stent valve's anchoring mechanism is derived from, for example, a funnel shape with a larger diameter at the free end and smaller diameter at the point where the covered portion meets the uncovered portion.

In a second aspect, the stent graft provides:

a main body stent graft defining a lumen having a first end and a second end;

a diaphragm coupled to the main body stent graft, wherein the diaphragm defines at least three openings;

at least three stent graft extensions each defining a lumen, wherein a first end of each of the at least three stent graft extensions is coupled to one of the at least three openings;

a visceral-vessel opening defined in a sidewall of the main body stent graft between the first end and the second end of the main body stent graft, wherein the diaphragm is disposed within the lumen of the main body stent graft, wherein the at least three openings of the diaphragm comprise a first opening, a second opening, a third opening and a fourth opening; and a visceral chamber defined by a sidewall coupled to one of the second opening and the diaphragm and to one of the visceral-vessel opening and the sidewall of the main body stent graft.

Referring now to FIGS. 1-6, a stent graft 100 is shown including a main body stent graft 105 defining a lumen having an inlet 106 defined at a first or proximal end 107 of the main body stent graft 105 and having an outlet 108 defined at a second or distal end 109 of the main body stent graft 105. In one embodiment, a portion of the lumen of the main body stent graft 105 arranged between the diaphragm 110 and the proximal end 107 of the main body stent graft 105 may have a diameter ranging from about 20 mm to about 65 mm and preferably from about 20 mm to about 46 mm. In another embodiment, the main body stent graft 105 may have a length ranging from about 10 mm to about 150 mm extending between the first end 107 of the main body stent graft 105 and the first end 116 of the visceral-vessel opening 115. In a further embodiment, the main body stent graft 105 may have a length ranging from 0 mm to about 40 mm extending between the second or distal end 117 of the visceral-vessel opening 115 and the second end 109 of the main body stent graft 105.

Figure 6:
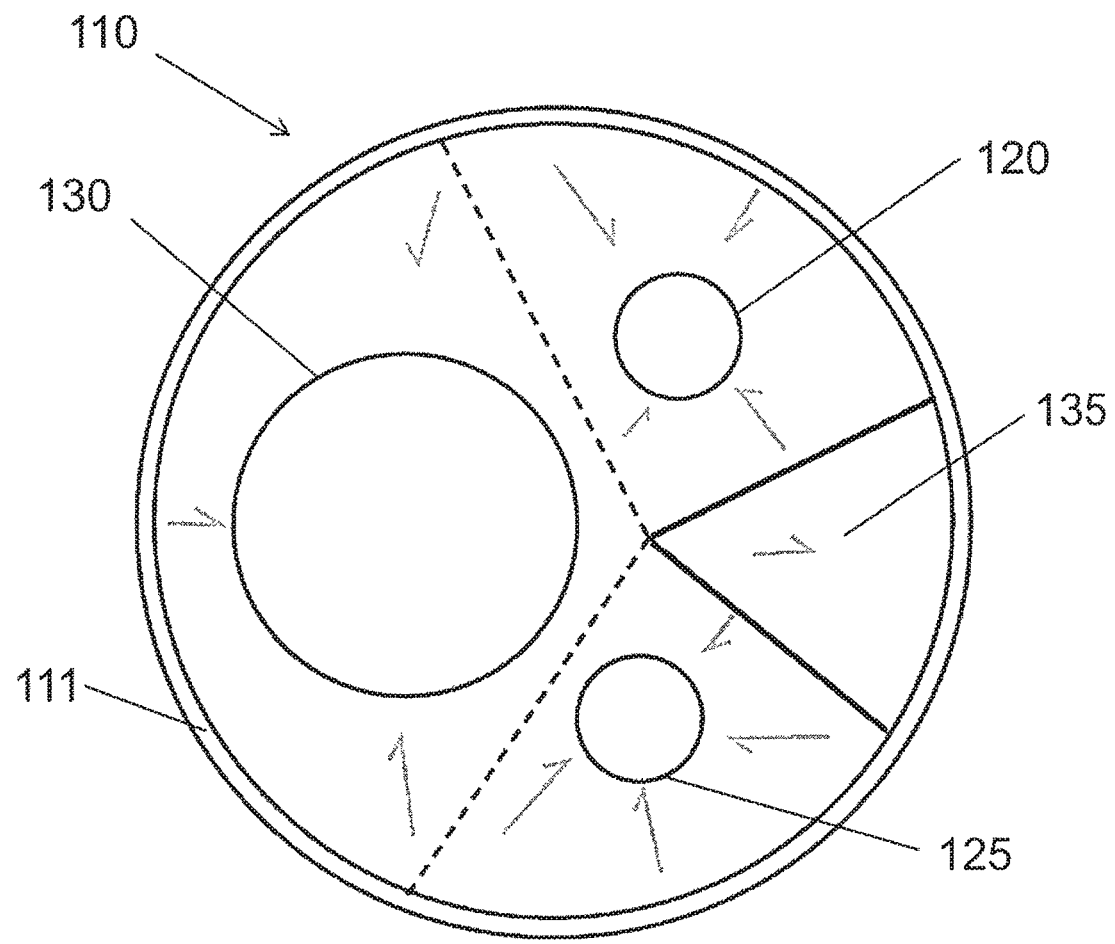
FIG. 6 is a top view of the stent graft according to the example embodiment of FIG. 1.

The stent graft 100 includes a diaphragm 110 disposed within the lumen of the main body stent graft 105 and coupled to the main body stent graft 105. The diaphragm 110 defines a first opening 130, a second opening 135, a third opening 120 and a fourth opening 125. In one embodiment, the first opening 130 may be used to stent the infrarenal segment, the second opening 135 may be used stent the celiac and SMA arteries, the third opening 120 and the fourth opening 125 may be used to stent the renal arteries. The second opening 135 may be aligned in a quadrant of the diaphragm 110 that lies above the visceral-vessel opening 115, discussed in more detail below, and the first opening 130 and the third and fourth openings 120, 125 may be arranged in various configurations in the same or other quadrants of the diaphragm 110. For example, in one embodiment, as shown in FIG. 6, the first opening 130 and the second opening 135 may be arranged on opposite sides of the diaphragm 110 with the third opening 120 and the fourth opening 125 likewise arranged on opposite sides of the diaphragm 110 between the first opening 130 and the second opening 135. Alternatively, the third and fourth openings 120, 125 may be arranged on the same side of the diaphragm 110 between the first opening 130 and the second opening 135. In other embodiments, the first opening 130 and one of the third and fourth openings 120, 125 and may be arranged on opposite sides of the diaphragm 110 with the other opening arranged therebetween. In a further embodiment, the first opening 130 and the third and fourth openings 120, 125 may be arranged such that there is no other inlet directly opposite the second opening 135.

In one embodiment, the diaphragm 110 may be sloped or tapered in the regions surrounding these various openings. In one embodiment, the second opening 135 may be defined as a V-shape, a half-circle having a radius ranging from about 5 mm to about 15 mm or a complete circular opening with a diameter ranging from about 6 mm to about 20 mm, among other possibilities. In further embodiments, the third opening 120, fourth opening 125, first opening 130 may have a substantially circular shape. In one embodiment, three stent graft extensions 121, 126 and 131 may be directly coupled to the third opening 120, the fourth opening 125 and the first opening 130, respectively, in fluid-tight (blood-tight) manner prior to deployment of the stent graft 100. These stent graft extensions 121, 126, 131 each define a lumen and are configured to receive extension or bridging stent grafts that may be held in place via passive or active fixation. This arrangement may provide blood flow between the stent graft 100 and the renal arteries and or may provide blood flow to the infrarenal arteries including, for example, the aorta and the common iliac arteries.

In various embodiments, the stent graft extensions 121, 126, 131 may be straight or gradually sweeping and their distal free ends 123, 128, 133 may be freely movable to place bridging stent grafts. In one embodiment, the stent graft extension 131 coupled to the first opening 130 may have a length of at least 30 mm and, in another embodiment, may have a length that ranges from about 10 mm to 120 mm.

And in another embodiment, the stent graft extension 131 may have a diameter ranging from about 8 mm to about 25 mm. In another embodiment, the first opening 130 may have a diameter ranging from about 8 mm to about 25 mm. In yet another embodiment, the diameter of the first opening 130 may be larger than the diameter of the stent graft extension 131 coupled thereto such that a first or proximal end of the stent graft extension 131 is tapered 132. In other embodiments, the third and fourth openings 120, 125 may each have a diameter ranging from about 4 mm to about 25 mm. In one embodiment, the stent graft extensions 121, 126 coupled to the third and fourth openings may each have a diameter ranging from about 4 mm to about 18 mm. In a further embodiment, the diameter of each of the third and fourth openings 120, 125 may be larger than the diameter of each of the stent graft extensions 121, 126 coupled thereto such that a first or proximal end of each of the stent graft extensions 121, 126 is tapered 122, 127. Tapering from the diaphragm openings to the various stent graft extensions may aid with guidewire alignment and entry into the respective lumens to place extension or bridging stents and may encourage laminar blood flow. In another embodiment, the stent graft extensions 121, 126 and 131 may be placed separately after deployment. In this embodiment, the stent graft extensions 121, 126, 131 may have flared proximal ends that are arranged proximal of the diaphragm upon deployment.

In one embodiment, a pair of opposing helical stent structures may be coupled to and extend along the length of one or more of the stent graft extensions 121, 126 and 131. The helical stent structures may advantageously prevent elongation of the lumens. These helical stent structures may be made from biocompatible materials with elastic shape memory, such as nitinol, stainless steel, plastics, polymers or any combination of such materials, among other possibilities.

In a further embodiment, according to the first, second and third aspects of the present disclosure, the diaphragm 110 may have an expandable frame 111. This expandable frame 111 may be configured to apply an outward radial force to the main body stent graft 105 in response to a downward force applied to the diaphragm 110. The downward force may be due to blood flow, for example. In one embodiment, the diaphragm 110 may be positioned within the lumen of the main body stent graft 105 at or between a first end 116 of the visceral-vessel opening 115 and a second end 117 of the visceral-vessel opening 115.

The stent graft 100 also includes a visceral-vessel opening 115 defined in a sidewall 118 of the main body stent graft 105 between the first end 107 and the second end 109 of the main body stent graft 105. In one embodiment, the visceral-vessel opening 115 may have a height ranging from about 10 mm to about 60 mm and may have a width ranging from about 5 mm to about 30 mm. In one embodiment, the visceral-vessel opening may be wider at a first or proximal end than at a second or distal end, which may provide more graft surface area between the visceral-vessel opening 115 and two renal openings 170 to provide a more robust seal between the stent graft and vasculature. In another embodiment, the visceral-vessel opening 115 may be covered with a flow-diverting material, for example, a high pick density braided or woven self-expanding stent material. This flow-diverting material may allow patency to the visceral vessels, for example, while minimizing the degree of unstented aortic wall to aid in anchoring and seal between the para-renal stent graft within vasculature. This may provide a more robust seal between the stent graft and aorta. The flow-diverting material may also permit formation of thrombus and arterial development therethrough, which may aid in appropriate blood flow and blood pressure through this region of the main body stent graft 105.

In addition, the stent graft 100 includes a visceral chamber 140 defined by a sidewall 141 coupled to one of the diaphragm 110 and the second opening 135 and to one of the sidewall of the main bode stent graft and the visceral-vessel opening. The visceral chamber 140 may provide blood flow to the SMA and celiac arteries. In addition, a surgeon may utilize the visceral chamber 140 to place bridging stents in the SMA and/or celiac arteries In one embodiment, the stent graft 100 may further include a plurality of sealing rings coupled to the main body stent graft 105. In another embodiment, the plurality of sealing rings may include a proximal sealing ring 145 coupled to the main body stent graft 105 at or directly adjacent to the first end 107 of the main body stent graft 105. In a further embodiment, the proximal sealing ring 145 may have a bi-level construction defining an upper portion 146 and a lower portion 147. The lower portion 147 of the proximal sealing ring 145 may be aligned with and arranged proximal to the visceral-vessel opening 115, and the lower portion 147 may be arranged distal to the upper portion 146 of the proximal sealing ring 145. In one embodiment, the upper portion 146 of the proximal sealing ring 145 may be longitudinally spaced apart from the lower portion 147 along the main body stent graft 105 by a distance ranging from about 0 mm to about 40 mm. In the bi-level embodiment, a peripheral edge 104 of the first end 107 of the main body stent graft 105 may have the same bi-level contour as the proximal sealing ring 145. In one embodiment, the main body stent graft 105 may have a length ranging from about 0 mm to about 20 mm extending between the lower portion 147 of the proximal sealing ring 145 of the main body stent graft 105 and the first end 116 of the visceral-vessel opening 115.

The graft material of the main body stent graft 105 may have the same boundary as the proximal sealing ring 145 to avoid covering the lumbar arteries that deliver blood to the spine. In other embodiments, the graft material may have a uniform circumference along the upper boundary of the proximal sealing ring 145. In still further embodiments, the graft material may extend beyond the upper proximal boundary of the proximal sealing ring 145 to the top or proximal edge of a fixation stent 150.

In another embodiment, the plurality of sealing rings may include a visceral-vessel sealing ring 155 coupled to the main body stent graft 105 such that the visceral-vessel sealing ring 155 surrounds the visceral-vessel opening 115. For example, the visceral-vessel sealing ring 155 may apply a circumferential force to keep the visceral-vessel opening 115 intact upon deployment providing a fluid tight seal about the SMA and celiac arteries. The plurality of sealing rings may also include at least one support sealing ring 160 coupled to the main body stent graft 105 such that a first end 161 of the at least one support sealing ring 160 is coupled to a first side of the visceral-vessel sealing ring 155 and a second end 162 of the at least one support sealing ring 155 is coupled to a second side of the visceral-vessel sealing ring 155. The visceral-vessel sealing ring 155 may also work in combination with the support sealing ring 160 to provide a circumferential radial force relative to the main body stent graft 105 to provide a fluid tight (i.e., blood-tight) seal with the aorta, for example. In a further embodiment, the at least one support sealing ring 160 may include a proximal support sealing ring 163, a distal support sealing ring 164 and a central support sealing ring 160. In one embodiment, the central support sealing ring 160 may be coupled to the visceral vessel sealing ring 155. The proximal support sealing ring 163 may be coupled to the main body stent graft 105 between the first end 107 of the main body stent graft 105 and the central support sealing ring 160. And the distal support sealing ring 164 may be coupled to the main body stent graft 105 between the second end 109 of the main body stent graft 105 and the central support sealing ring 160.

In still another embodiment, the plurality of sealing rings may include a distal sealing ring 165 coupled to the main body stent graft 105 at or directly adjacent to the second end 109 of the main body stent graft 105. In one embodiment, two renal openings 170 may be defined in the sidewall 118 of the main body stent graft 105 distal to the diaphragm 110. In one embodiment, the distal sealing ring 165 may have two radial portions 166 joined by two arch portions 167. The two arch portions 167 may be arranged longitudinally along the sidewall 118 of the main body stent graft 105 and the two radial portions 166 are arranged about the circumference of the main body stent graft 105. The two arch portions 167 are aligned with the two renal openings 170. In one embodiment, an effective diameter extending between the two radial portions 166 of the distal sealing ring 165 may range from about 20 mm to about 50 mm. In one embodiment, the two arch portions 167 may have a width ranging from about 4 mm to about 30 mm. In an embodiment in which renal openings 170 are not provided in the sidewall 118 of the main body stent graft 105, the length of the main body stent graft 105 may be shortened to permit the renal stent grafts to exit from the second end 109 such that they are able to have a gentle sweep or large radius of curvature from the renal inlet and the target vessel ostium when bridging stents are placed. In still another embodiment, shown in FIGS. 7A-8B, the two renal openings 170 in the sidewall of the main body stent graft may be fenestrations sized and shaped to allow access to the native arteries.

In one embodiment, applicable to the first, second and third aspects of the present disclosure, a bridging stent graft may comprise spaced-apart stent rings coupled to two wires longitudinally disposed along the length of and on opposite sides of the bridging stent graft in a helical shape. This arrangement may beneficially prevent elongation of the bridging stent graft. An appropriate overlap with the stent graft extensions 121, 126 coupled to the third and fourth openings 120, 125 or stent graft extension 131 coupled to the first opening 130 may be adequate to achieve passive fixation with a bridging stent graft during stent graft debranching procedures. The length of this overlap region may be less if active fixation features are also employed with the stent grafts, for example.

In a third aspect, the stent graft provides:
  a main body stent graft defining a lumen having a first end and a second end;
  a diaphragm coupled to the main body stent graft, wherein the diaphragm defines at least three openings; and
  at least three stent graft extensions each defining a lumen, wherein a first end of each of the at least three stent graft extensions is coupled to one of the at least three openings; and
  a visceral-vessel opening defined in a sidewall of the main body stent graft between the first end and the second end of the main body stent graft, wherein the diaphragm is disposed within the lumen of the main body stent graft, and wherein the at least three openings of the diaphragm comprise a first opening, a second opening, a third opening and a fourth opening.

Figure 7A:
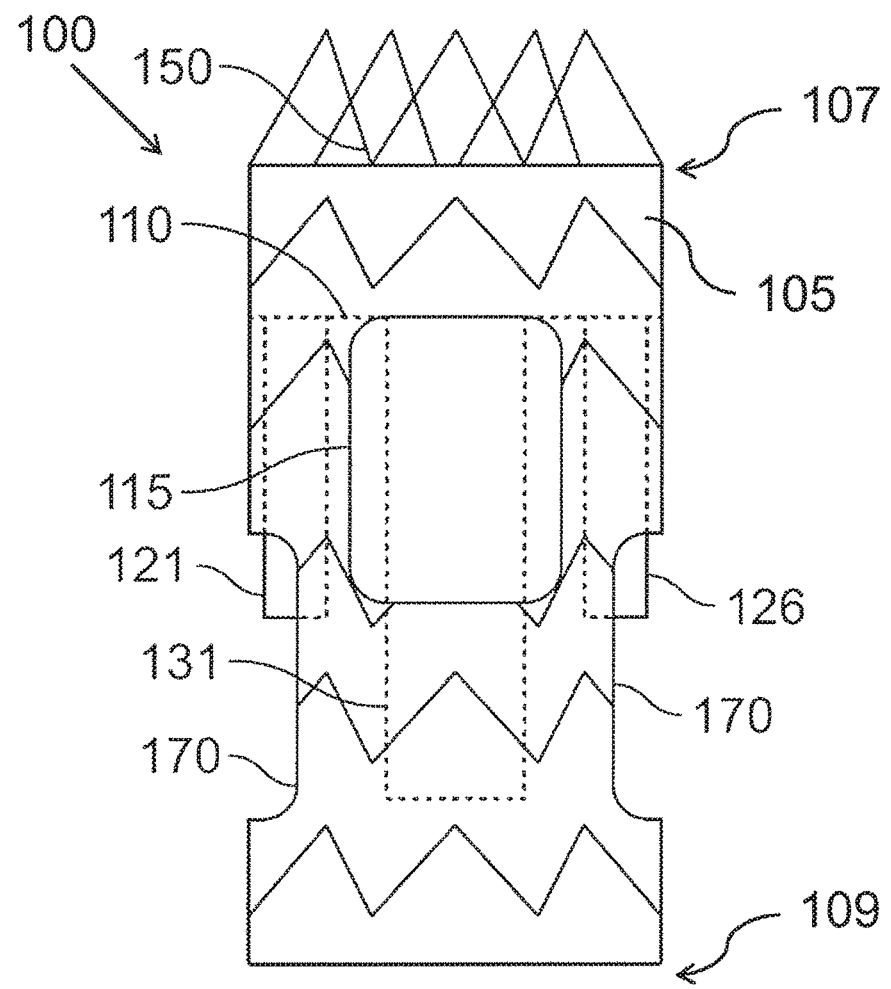
FIG. 7A is a front view of the stent graft according to a second example embodiment.
Figure 7B:
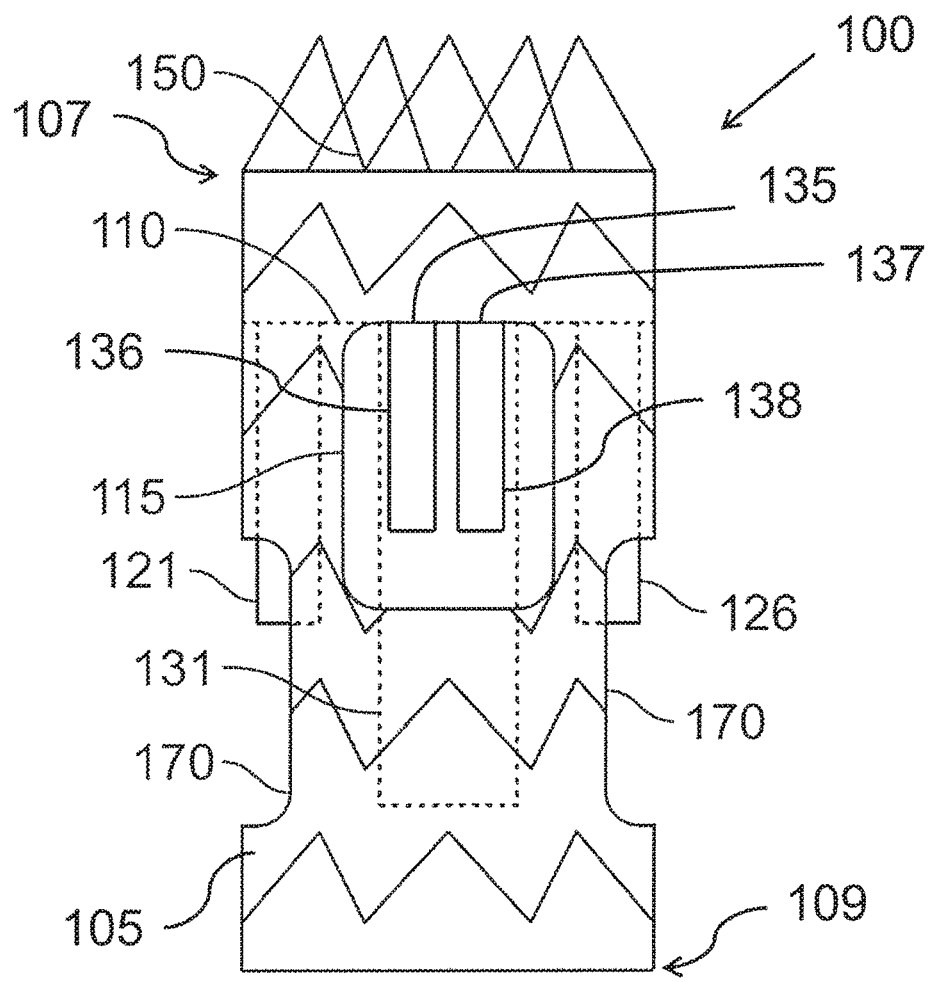
FIG. 7B is a front view of the stent graft according to the second example embodiment having a fifth opening coupled to stent extension graft.
Figure 8A:
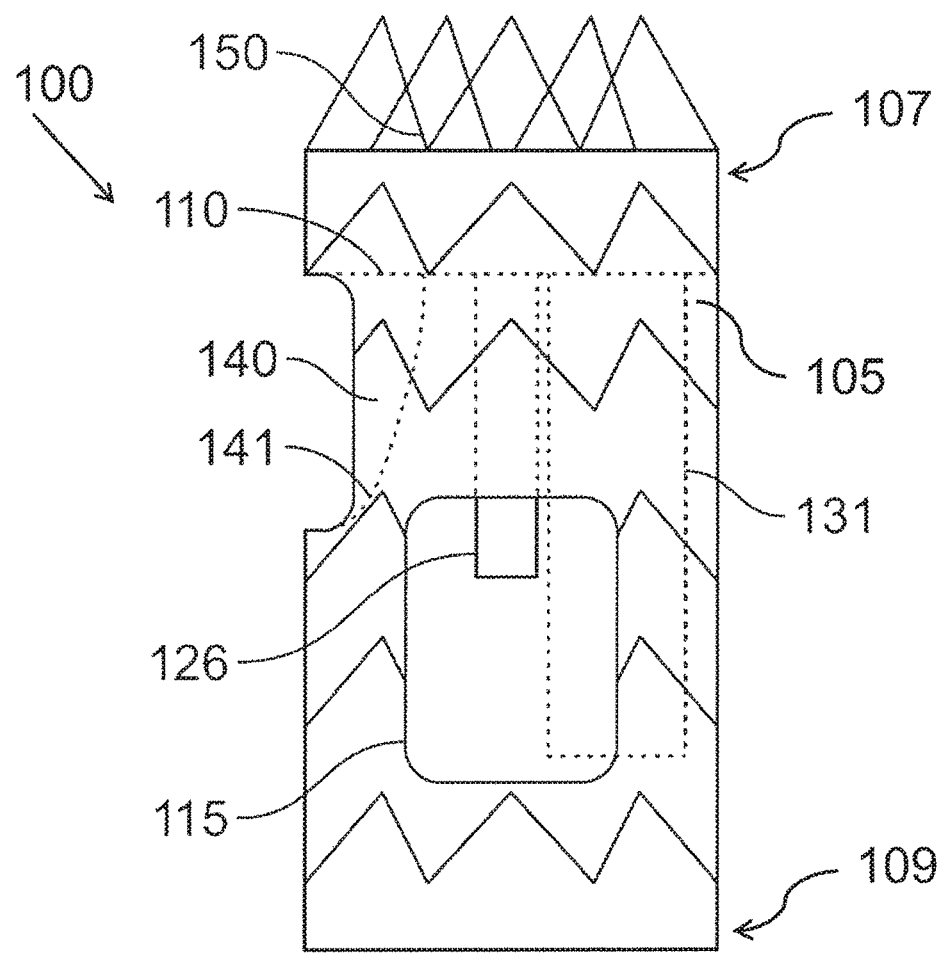
FIG. 8A is a side view of the stent graft according to the example embodiment of FIG. 7A.
Figure 8B:
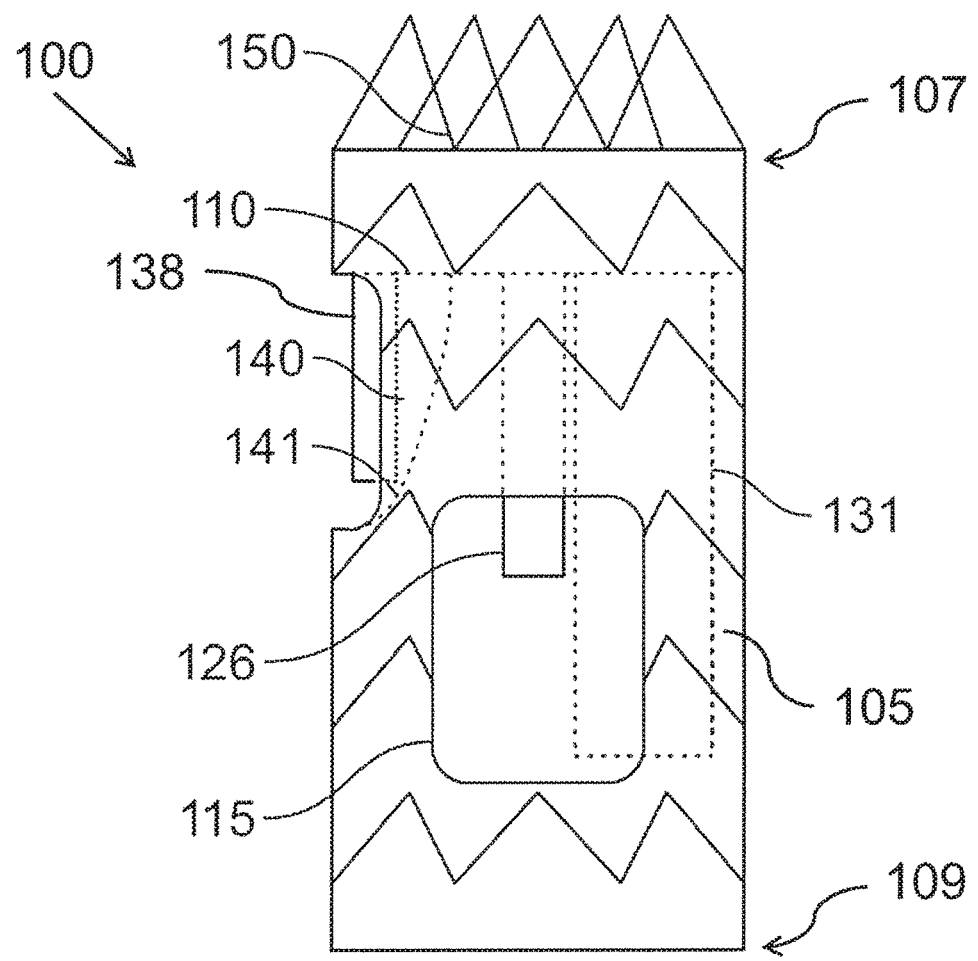
FIG. 8B is a side view of the stent graft according to the example embodiment of FIG. 7B.

Referring now to FIGS. 7A and 7B, a stent graft 100 is shown including a main body stent graft 105 defining a lumen having first end 107 and a second 109 that may correspond to a proximal end and a distal end, respectively, in one embodiment. A visceral-vessel opening 115 is defined in a sidewall of the main body stent graft 105 between the first end 107 and the second end 109 of the main body stent graft 105. In addition, a diaphragm 110 is disposed within the lumen of the main body stent graft 105 and coupled to the main body stent graft 105. The diaphragm defines a first opening, a second opening, a third opening and a fourth opening. In one embodiment, each of the openings may receive a bridging stent, for example, and couple the infra-renal segment to the first opening 130, couple the celiac and SMA arteries to the second opening 135 and couple the couple the renal arteries to the third and fourth openings 120, 125.

In one embodiment, a visceral chamber 140 may be defined by the diaphragm 110, the sidewall of the main body stent graft 105 and a visceral sidewall 141 extending between the diaphragm 110 and the sidewall of the main body stent graft 105. In another embodiment, a fifth opening 137 is defined in the diaphragm between the visceral sidewall and the sidewall of the main body stent graft 105. This fifth opening 137 may beneficially permit blood flow to the celiac and SMA arteries while the second opening 135 is being actively stented or otherwise blocked and vice versa. The fifth opening 137 may also allow for more than one of the celiac and SMA arteries to be bridged with stents grafts.

The second and fifth openings 135, 137 are defined in the diaphragm 110 between the visceral sidewall 141 and the sidewall of the main body stent graft 105. The visceral sidewall 141 surrounds a portion of the visceral-vessel opening 115 defined between the second end 109 of the main body stent graft 105 and the diaphragm 110.

In one embodiment, the second opening 135 and the fifth opening 137 may be arranged adjacent to each other. In another embodiment, the second opening 135 may be coupled to a stent graft extension 136 defining a lumen, and the fifth opening 137 may also be coupled to a stent graft extension 138 defining a lumen. In further embodiments, each of the stent graft extensions coupled to one of the second and fifth openings may have a diameter ranging from about 6 mm to about 14 mm and may have a length ranging from about 0.5 mm to about 40 mm.

In a further embodiment, one or more of the first 130, second 135, third 120, fourth 125 and fifth 137 openings may be reinforced.

Figure 24:
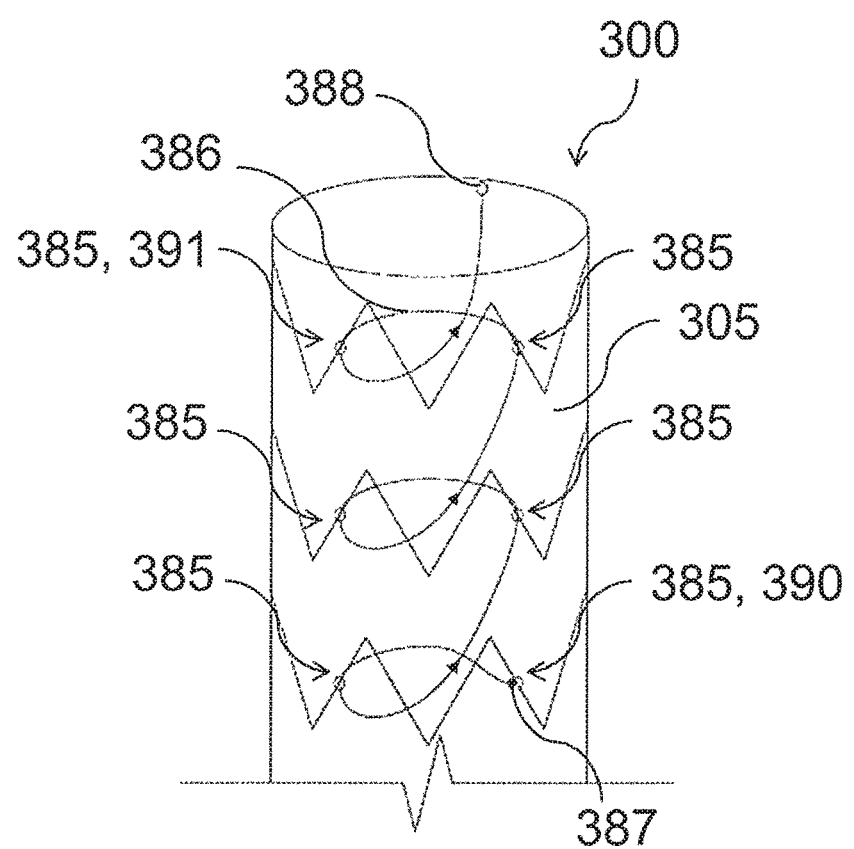
FIG. 24 is a side view of the stent graft according to a seventh example embodiment.
Figure 25A:
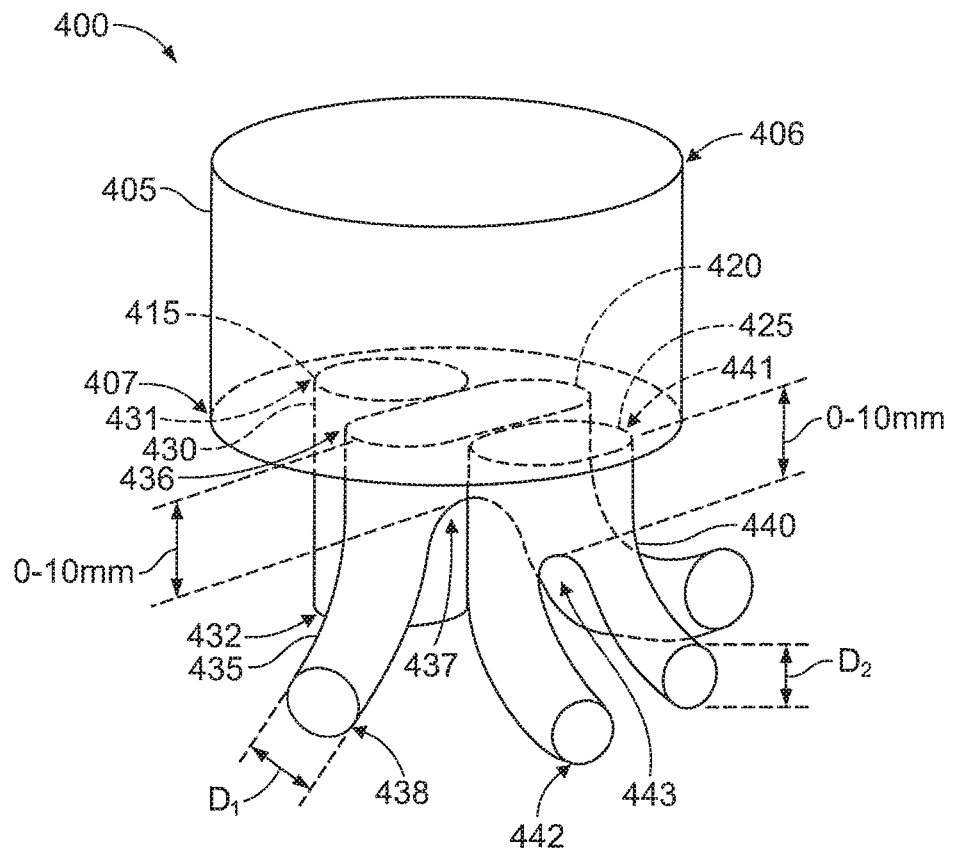
FIG. 25A is a perspective view of the stent graft according to an eighth embodiment.
Figure 25B:
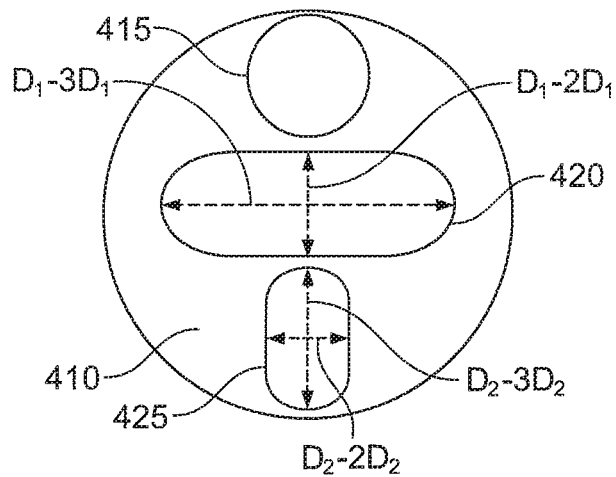
FIG. 25B is a top view of the stent graft according to the example embodiment of FIG. 25A.

In one embodiment, shown in FIG. 24 and applicable to all of the aspects of the present disclosure, the stent graft 300 includes a plurality of anchors 385 that each define an eyelet. The plurality of anchors 385 are arranged longitudinally at intervals along the main body stent graft 305. In a further embodiment, the stent graft 300 includes a string 386 having a first end 387 and a second end 388. The string 386 may be slidably disposed through the eyelets of the plurality of anchors 385 such that the main body stent graft 305 has a partially-expanded condition and a fully-expanded condition. In the partially-expanded condition, the string 386 may be under tension and the first end 387 of the string may be fixedly coupled to a first anchor 390 of the plurality anchors 385 and the second end 388 of the string 386 may be releasably coupled to a second anchor 391 of the plurality of anchors. In the fully-expanded condition (see FIG. 24), the second end of the string 388 may be released from the second anchor 391 and the string 386 may be untensioned.

In one embodiment, the main body stent graft 305 may expand from 50% to 95% of the fully-expanded diameter in the partially-expanded condition. As such, the partially-expanded condition may enable the stent graft to be deployed into a lumen and then subsequently repositioned. For example, the smaller diameter of the partially-expanded stent graft may permit the stent graft to be moved proximally and distally to the desired location in the lumen and rotated for alignment with appropriate branch vasculature. Once in position, the releasable end 388 of the string 386 may be decoupled from an anchor 391, as described below, and the stent graft 300 may transition into the fully-expanded condition due to shape memory of stents or balloon expansion, for example.

In another embodiment, the plurality of anchors may be arranged on a side of the main body stent graft opposite to a visceral-vessel opening. In a further embodiment, the plurality of anchors may be arranged as laterally opposed pairs (see FIG. 24). In another embodiment, the plurality of anchors may be arranged in a zig-zag pattern.

In one embodiment, the eyelets of the plurality of anchors 385 and the string 386 may be made of a low-friction material to enable the stent graft 300 to transition from the partially-expanded condition to the fully-expanded condition.

The stent grafts of the present disclosure may contain any further suitable components, including but not limited to radiopaque markers to aid in visualization and to facilitate accurate placement of the stent graft. These radiopaque markers may take the form of gold bands at the distal end of each individual lumen of a given stent graft or a directional marker, for example in the shape of an "S" or any other suitable form for indicating direction and orientation of the stent graft. In one embodiment, the first or proximal end 107, 207 of the main body stent graft 105 may be coupled to a fixation stent 150. In addition, bi-directional anchoring hooks may be formed as part of the fixation stent 150 may be utilized to gain solid purchase in the non-diseased portion of a vessel wall. This fixation stent 150 may provide for radial-force fixation within the vessel in conjunction with bidirectional hooks. In another embodiment, the fixation stent 150 may be biased away from the lumen of the main body stent graft 105 to maintain fixation with vasculature in a deployed condition even if an aneurysm advances proximally.

In a fourth aspect, the invention provides a method for placement of the stent graft 100 according to the first aspect of the invention. The method includes (a) introducing a guidewire into any appropriately sized arterial configuration via arterial access, (b) loading a delivery catheter containing the stent graft of any of the foregoing embodiments onto the guidewire, (c) moving the delivery catheter along the guidewire and introducing the delivery catheter into the appropriately sized arterial configuration via arterial access and (d) deploying the stent graft into the appropriately sized arterial configuration and/or a lumen of a previously-placed stent graft.

In one embodiment, the method may further include maintaining the stent graft in a partially-compressed condition via a tensioned string disposed through a plurality of anchors that each define an eyelet. In one embodiment, the tension on the string may be reduced by releasing one end of the wire from a first anchor of the plurality of anchors. Once tension on the string is reduced, the stent graft may then expand into the fully-expanded condition.

In one embodiment, the second aspect may further include (e) loading a second delivery catheter containing a bridging stent graft onto the guidewire, (f) moving the second delivery catheter along the guidewire and introducing the second delivery catheter into the proximal end 107 of main body lumen of the stent graft 105 via arterial access, (g) selecting from among the first renal inlet 120, the second renal inlet 125, the infrarenal inlet 130 or the visceral inlet 135 defined in the diaphragm 110, (h) introducing the second delivery catheter into the selected inlet and into either a lumen 121, 126, 131 coupled to the selected inlet or an appropriately sized arterial lumen and (i) deploying all or a portion of the bridging stent graft into the selected inlet or the appropriately sized arterial lumen.

In a fifth aspect, a stent graft provides:
  a main body stent graft defining a lumen having a first end and a second end;
  a diaphragm coupled to the main body stent graft, wherein the diaphragm defines a first opening, a second opening and a third opening;
  a first stent graft extension having a first end and a second end, wherein the first stent graft extension has a single lumen, wherein the first end of the first stent graft extension is coupled to the diaphragm and arranged surrounding the first opening;
  a second stent graft extension having a first end and a second end, wherein the second stent graft extension has a single lumen at the first end and has a bifurcation defining two lumens at the second end, wherein the first end of the second stent graft extension is coupled to the diaphragm and arranged surrounding the second opening; and
  a third stent graft extension having a first end and a second end, wherein the third stent graft extension has a single lumen at the first end, wherein the first end of the third stent graft extension is coupled to the diaphragm and arranged surrounding the third opening.

Referring now to FIGS. 25A-26B, a stent graft 400 is shown having a main body stent graft 405 defining a lumen having a first end 406 and a second end 407. Coupled to the main body stent graft 405 is a diaphragm 410 that defines a first opening 415, a second opening 420 and a third opening 425. A first stent graft extension 430 defines a single lumen and has a first end 431 and a second end 432, and the first end 431 of the first stent graft extension 430 is coupled to the diaphragm 410 and arranged surrounding the first opening 415. A second stent graft extension 435 has a single lumen at a first end 436 and has a bifurcation 437 defining two lumens at the second end 438. The first end 436 of the second stent graft extension 435 is coupled to the diaphragm 410 and arranged surrounding the second opening 420. And a third stent graft extension 440 has a first end 441 and a second end 442. The third stent graft extension 440 has a single lumen at the first end 441, and the first end 441 of the third stent graft extension 440 is coupled to the diaphragm 410 and arranged surrounding the third opening 425.

Figure 26A:
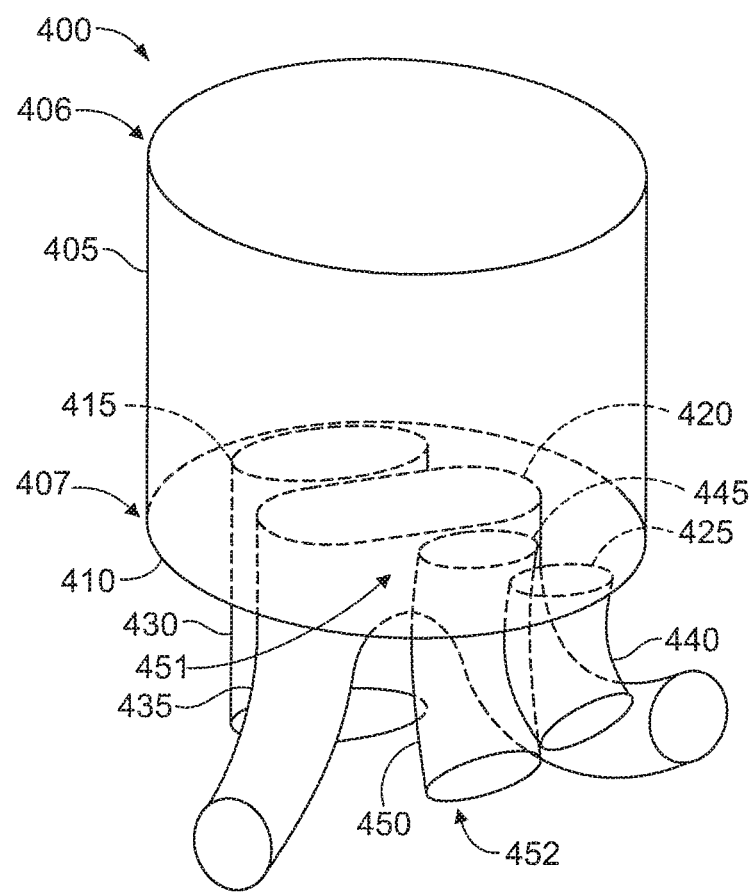
FIG. 26A is a perspective view of the stent graft according to a ninth embodiment.
Figure 26B:
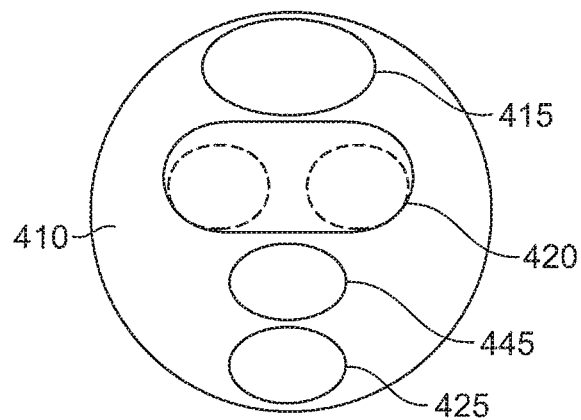
FIG. 26B is a top view of the stent graft according to the example embodiment of FIG. 26A.

In one embodiment, shown in FIGS. 26A-B, the first opening 415 may be circular, the second opening 420 may be elliptical and the third opening 425 may be circular. In this embodiment, the stent graft 400 may further include a fourth opening 445 defined in the diaphragm 410 that is circular. And a fourth stent graft extension 450 having a first end 451 and a second end 452, wherein the fourth stent graft extension 450 has a single lumen at the first end 451, and the first end 451 of the fourth stent graft extension 450 is coupled to the diaphragm 410 and arranged surrounding the fourth opening 445. In one embodiment, the third opening 425 and the fourth opening 445 may be arranged adjacent to each other. In alternative embodiments (not shown), the first opening may be circular, the second opening may be circular and the third opening may be elliptical. In a further embodiment, a fourth opening may be defined in the diaphragm that is circular and located adjacent to the second opening.

In another embodiment, the first opening 415 is circular, the second opening 420 is elliptical and the third opening 425 is elliptical. The third stent graft extension 440 may have a bifurcation 443 defining two lumens at the second end 442. In one embodiment, the second opening 420 is arranged between the first opening 415 and the third opening 425. In a further embodiment, a major axis of the second opening 420 may be arranged perpendicular to the major axis of the third opening 425. In yet another embodiment, a minor axis of the second opening 420 is aligned with the major axis of the third opening 425.

In one embodiment, the two lumens of the second stent graft extension 435 each have a diameter ranging from about 4 mm to about 12 mm. In another embodiment, a major axis of the second opening 420 may have a length ranging from about 4 mm to about 36 mm, and a minor axis of the second opening 420 may have a length ranging from about 4 mm to about 24 mm.

In another embodiment, the two lumens of the third stent graft extension 440 may each have a diameter ranging from about 6 mm to about 14 mm. In a further embodiment, a major axis of the third opening has a length ranging from about 6 mm to about 42 mm, and wherein a minor axis of the third opening has a length ranging from about 6 mm to about 28 mm.

In a still further embodiment, the bifurcation 437 of the second stent graft extension 435 may occur at a location ranging from about 0 mm to about 50 mm from the diaphragm 410 and the bifurcation 443 of the third stent graft extension 440 occurs at a location ranging from about 0 mm to about 50 mm from the diaphragm 410. In some embodiments, recessing the bifurcation away from the diaphragm may create a cavity that permits selection of one of the two lumens of the second and third graft extensions via an articulable catheter tip. This may help reduce the time it takes to advance a bridging stent into place, thereby reducing the amount of fluorescence and radiation used to visualize device placement during surgery. In another embodiment, the first stent graft extension 430, the second stent graft extension 435 and third stent graft extension 440 may each have a length ranging from about 5 mm to about 50 mm.

In one embodiment, the first end 438 of the second stent graft extension 435 is tapered, and the first end 441 of the third stent graft extension 440 is tapered. In a further embodiment, the first end 431 of the first stent graft extension 430 is tapered.

In a sixth aspect, a stent graft provides:
  a main body stent graft defining a lumen having a first end and a second end;
  a diaphragm coupled to the main body stent graft within the lumen, wherein the diaphragm defines at least three openings;
  at least three stent graft extensions each defining a lumen, wherein a first end of each of the at least three stent graft extensions is coupled to one of the at least three openings;
  a visceral vessel opening defined in the sidewall of the main body stent graft;
  two renal openings defined in the sidewall of the main body stent graft distal to the diaphragm; and
  permeable membrane material covering at least one of the visceral vessel opening and the two renal openings.

Figure 27A:
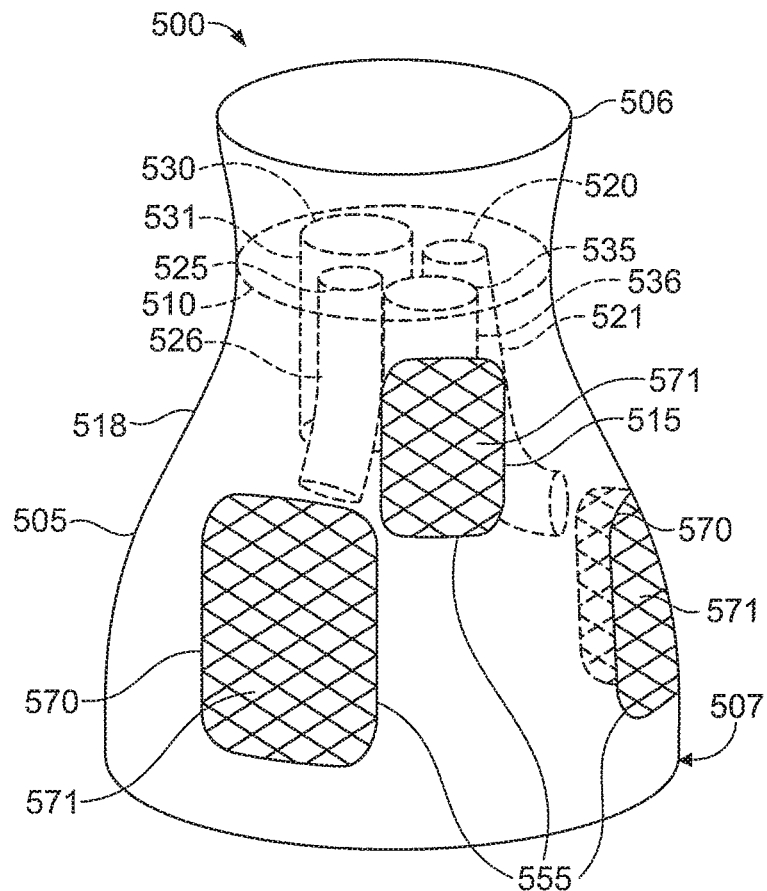
FIG. 27A is a perspective view of the stent graft according to a sixth aspect.
Figure 27B:
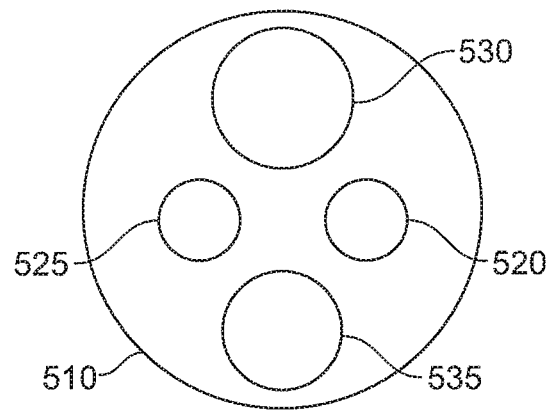
FIG. 27B is a top view of the stent graft according to the example embodiment of FIG. 27A.

Referring now to FIGS. 27A-B, a stent graft 500 is shown having a main body stent graft 505 that defines a lumen with a first end 506 and a second end 507. A diaphragm 510 is coupled to the main body stent graft 505 within the lumen, and the diaphragm 510 defines at least three openings. In the embodiment shown, the diaphragm 510 has four openings, namely a first opening 530, a second opening 535, a third opening 520 and a fourth opening 525. Stent graft 500 also includes stent graft extensions 521, 526, 531, 536 each having a first end coupled to one of the openings 520, 525, 530, 535, respectively, and each defining a lumen. A visceral vessel opening 515 is defined in the sidewall 518 of the main body stent graft 505. Two renal openings 570 are also defined in the sidewall 515 of the main body stent graft 505 distal to the diaphragm 510. A permeable membrane material 571 covers at least one of the visceral vessel opening 518 and the two renal openings 570.

In one embodiment, the permeable membrane material 571 may be perforable. For example, a catheter, a guidewire, a bridging stent graft or other implement may be used to perforate the permeable membrane material 571. In operation, a bridging stent graft may be placed through the perforation in the permeable membrane material 571 such that there is seal between the bridging stent graft and the permeable membrane material 571. In a further embodiment, the permeable membrane material 571 may be configured to be sealed via thrombosis in vivo. In another embodiment, the permeable membrane material 571 may include, but is not limited to, one or more of nitinol, polytetrafluoroethylene ("PTFE"), polyester, nonabsorbale polymer and combinations thereof. Still further, the permeable membrane material 571 may be woven, mesh, or electrospun, for example.

In another embodiment, the second end 507 of the main body stent graft 505 may be arranging distal with respect to bloodflow, such that bloodflow enters the first end 506 and exits the second end 507. The diameter of the main body stent graft 505 at the second end 507 may be greater than the diameter of the main body stent graft 505 at the first end 506. This arrangement may help anchor the stent graft 500 against the aortic wall and resist migration due to bloodflow. In a further embodiment, the second end 507 of the main body stent graft 505 is bell-shaped, as shown in FIG. 27A in an expanded ex vivo condition.

In one embodiment, the stent graft may include one or more sealing rings 555 coupled to the main body stent graft 505 surrounding one or more of the two renal openings 570 and the visceral vessel opening 518.

In one embodiment, the two renal openings 570 may be fenestrations. In another embodiment, the two renal openings 570 may be two arch portions as described above with respect to the second aspect of the invention.

Various embodiments of the stent grafts according to the first, second, third, fifth and sixth aspects of the invention are shown in FIGS. 17-23 and 25A-27B in one of the visceral trunk or thoracic aorta after deployment in vivo according to the methods of the fourth aspect of the invention.

Although specific embodiments have been illustrated and described herein, it will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. The above embodiments and other embodiments may be combined as is apparent to those of skill in the art upon studying the above description, unless noted otherwise.

The invention claimed is:

1. A stent graft, comprising: a main body stent graft defining a lumen having a first end and a second end, wherein the first end of the main body stent graft is configured to be a proximal end and the second end of the main body stent graft is configured to be a distal end; a first stent graft extension having a first end and a second end, wherein the first stent graft extension has a single lumen, wherein the first end of the first stent graft extension is coupled to the second end of the main body stent graft; a second stent graft extension having a first end and a second end, wherein the second stent graft extension has a single lumen at the first end and has a bifurcation defining two lumens at the second end, wherein the first end of the second stent graft extension is coupled to the second end of the main body stent graft; and a third stent graft extension having a first end and a second end, wherein the third stent graft extension has a single lumen at the first end, wherein the first end of the third stent graft extension is coupled to the second end of the main body stent graft; and a diaphragm coupled to the main body stent graft at the second end of the lumen of the main body stent graft such that the first stent graft extension, the second stent graft extension and the third stent graft extension are arranged entirely external to the lumen of the main body stent graft and form a single unitary structure with the main body stent graft in both a pre-deployment ex vivo state and a deployed in vivo state, wherein the diaphragm defines a first opening, a second opening and a third opening, wherein the first end of the first stent graft extension is coupled to the diaphragm and arranged surrounding the first opening, wherein the first end of the second stent graft extension is coupled to the diaphragm and arranged surrounding the second opening, wherein the first end of the third stent graft extension is coupled to the diaphragm and arranged surrounding the third opening, wherein the first opening is circular and the second opening is elliptical and a minor axis of the second opening is larger than each diameter of the two lumens of the second stent graft extension, wherein the third opening is elliptical, wherein the second opening is arranged between the first opening and the third opening and wherein a major axis of the second opening is arranged perpendicular to a major axis of the third opening.

2. The stent graft of claim 1, further comprising:
   a fourth opening defined in the diaphragm, wherein the fourth opening is circular; and
   a fourth stent graft extension having a first end and a second end, the fourth stent graft extension has a single lumen at the first end and the first end of the fourth stent graft extension is coupled to the diaphragm and arranged surrounding the fourth opening.

3. The stent graft of claim 2, wherein the third opening and the fourth opening are arranged adjacent to each other.

4. The stent graft of claim 1, wherein the third stent graft extension has a bifurcation defining two lumens at the second end.

5. The stent graft of claim 4, wherein the two lumens of the third stent graft extension each have a diameter ranging from about 6 mm to about 14 mm.

6. The stent graft of claim 4, wherein a major axis of the third opening has a length ranging from about 6 mm to about 42 mm, and wherein the minor axis of the third opening has a length ranging from about 6 mm to about 28 mm.

7. The stent graft of claim 1, wherein the minor axis of the second opening is aligned with a major axis of the third opening.

8. The stent graft of claim 1, wherein the two lumens of the second stent graft extension each have a diameter ranging from about 4 mm to about 12 mm.

9. The stent graft of claim 1, wherein a major axis of the second opening has a length ranging from about 4 mm to about 36 mm, and wherein the minor axis of the second opening has a length ranging from about 4 mm to about 24 mm.

10. The stent graft of claim 1, wherein the bifurcation of the second stent graft extension occurs at a location ranging from about 0 mm to about 10 mm from the second end of the main body stent graft and wherein a bifurcation of the third stent graft extension occurs at a location ranging from about 0 mm to about 10 mm from the second end of the main body stent graft.

11. The stent graft of claim 1, wherein the first end of the second stent graft extension is tapered and wherein the first end of the third stent graft extension is tapered.

12. The stent graft of claim 1, wherein the first end of the first stent graft extension is tapered.

13. The stent graft of claim 1, wherein the first stent graft extension, the second stent graft extension and third stent graft extension each have a length ranging from about 5 mm to about 50 mm.

14. A method for placement of a stent graft, the method comprising:
    introducing a guidewire into any appropriately sized arterial configuration via arterial access;
    loading a delivery catheter containing the stent graft according to claim 1 onto the guidewire;
    moving the delivery catheter along the guidewire and introducing the delivery catheter into the appropriately sized arterial configuration via arterial access; and
    deploying the stent graft into the appropriately sized arterial configuration and/or a lumen of a previously-placed stent graft.

15. The method of claim 14, further comprising:
    loading a second delivery catheter containing a bridging stent graft onto the guidewire;
    moving the second delivery catheter along the guidewire and introducing the second delivery catheter into the first end of the lumen of the main body stent graft via arterial access;
    selecting from among the first opening, the second opening and the third opening defined in the diaphragm;
    introducing the second delivery catheter into the selected opening and into either a lumen coupled to the selected opening or an appropriately sized arterial lumen; and
    deploying all or a portion of the bridging stent graft into the selected opening or the appropriately sized arterial lumen.

* * * * *